(12) United States Patent
Davison

(10) Patent No.: US 11,890,394 B2
(45) Date of Patent: Feb. 6, 2024

(54) SURFACE TEXTURES OF MEDICAL DEVICES

(71) Applicant: Instructure Labs B.V., The Hague (NL)

(72) Inventor: Noel Lee Davison, The Hague (NL)

(73) Assignee: Instructure Labs B.V., The Hague (NL)

(*) Notice: Subject to any disclaimer, the term of this patent is extended or adjusted under 35 U.S.C. 154(b) by 157 days.

(21) Appl. No.: 17/675,326

(22) Filed: Feb. 18, 2022

(65) Prior Publication Data
US 2022/0265897 A1    Aug. 25, 2022

(30) Foreign Application Priority Data
Feb. 19, 2021 (NL) .................................. 2027599

(51) Int. Cl.
*A61F 2/00* (2006.01)
*A61L 27/34* (2006.01)
*A61L 31/04* (2006.01)

(52) U.S. Cl.
CPC .............. *A61L 27/34* (2013.01); *A61L 31/04* (2013.01); *A61F 2002/0086* (2013.01); *A61F 2240/005* (2013.01); *A61L 2430/04* (2013.01); *A61L 2430/16* (2013.01); *A61L 2430/20* (2013.01); *A61L 2430/22* (2013.01)

(58) Field of Classification Search
CPC ...... A61L 27/34; A61L 31/04; A61L 2430/04; A61L 2430/16; A61L 2430/20; A61L 2430/22; A61F 2002/0086; A61F 2240/005
See application file for complete search history.

(56) References Cited

U.S. PATENT DOCUMENTS

| | | | |
|---|---|---|---|
| 4,960,425 | A | 10/1990 | Yan et al. |
| 9,072,821 | B2 | 7/2015 | Van Epps et al. |
| 9,138,310 | B2 | 9/2015 | Powell et al. |
| 9,775,933 | B2 | 10/2017 | Knisley et al. |
| 9,808,338 | B2 | 11/2017 | Schuessler et al. |
| 10,232,081 | B2 | 3/2019 | Rotmans et al. |

(Continued)

FOREIGN PATENT DOCUMENTS

| WO | WO-9321858 A1 | * 11/1993 | ............. A61B 90/00 |
|---|---|---|---|
| WO | 2004008983 A1 | 1/2004 | |

(Continued)

OTHER PUBLICATIONS

"Geometrical product specifications (GPS)—Surface texture: Areal", ISO 25178-3, 2012, 1-33.

(Continued)

*Primary Examiner* — Jacqueline Woznicki
(74) *Attorney, Agent, or Firm* — N.V. Nederlandsch Octrooibureau

(57) ABSTRACT

One or more embodiments of the present invention are directed to a medical device having a textured surface with an arithmetical mean height value (Sa) below 3.0 μm and a developed interfacial area ratio (Sdr) above 1.0 and a density of peaks (Spd) above $1 \times 10^6$ peaks/mm$^2$; a process of preparing such a medical device using a microstructured template; and a method of treating a mammal with such a medical device.

20 Claims, 16 Drawing Sheets
(8 of 16 Drawing Sheet(s) Filed in Color)

(56) References Cited

U.S. PATENT DOCUMENTS

| | | | |
|---|---|---|---|
| 10,532,131 | B2 | 1/2020 | Yuan et al. |
| 10,595,979 | B2 | 3/2020 | Bayat et al. |
| 2006/0219143 | A1 | 10/2006 | Brennan et al. |
| 2010/0226943 | A1 | 9/2010 | Brennan et al. |
| 2011/0257623 | A1 | 10/2011 | Marshall et al. |
| 2011/0276134 | A1 | 11/2011 | Manesis et al. |
| 2013/0053956 | A1* | 2/2013 | Powell ............ A61F 2/12 623/8 |
| 2013/0110243 | A1 | 5/2013 | Patterson et al. |
| 2013/0190699 | A1 | 7/2013 | Stephan |
| 2015/0238306 | A1 | 8/2015 | Marshall et al. |
| 2016/0067382 | A1* | 3/2016 | Yuan ............ A61L 27/58 424/602 |
| 2017/0049549 | A1* | 2/2017 | Bayat ............ A61F 2/12 |
| 2020/0253738 | A1 | 8/2020 | De Boer et al. |
| 2020/0268499 | A1 | 8/2020 | Hill et al. |

FOREIGN PATENT DOCUMENTS

| | | |
|---|---|---|
| WO | 2009046425 A2 | 4/2009 |
| WO | 2011097499 A1 | 8/2011 |
| WO | 2016185186 A1 | 11/2016 |
| WO | 2018213390 A1 | 11/2018 |
| WO | 2019118983 A1 | 6/2019 |

OTHER PUBLICATIONS

"Geometrical product specifications (GPS)—Surface texture: Areal", ISO 25178-2, 2012, 1-54.

"Non-active surgical implants—Mammory implants—Particular requirements", ISO 14607, 2018, 1-48.

Blateyron, F., "The Areal Field Parameters. In: Leach R. (eds) Characterisation of Areal Surface Texture", Springer, Berlin, Heidelberg. https://doi-org.mu.idm.oclc.org/10.1007/978-3-642-36458-7_2, 2013, 1-355.

Davison, N. L., et al., "Submicron-Scale Surface Architecture of Tricalcium Phosphate Directs Osteogenesis in Vitro and in Vivo", ENULro Dpeaavnis Conel lest aanl.d Materials vol. 27, 2014, 281-297.

Grotendorst, Gary R., et al., "Combinatorial signaling pathways determine fibroblast proliferation and myofibroblast differentiation", FASEB J., vol. 18, 2004, 469-479.

Headon, Hannah, et al., "Capsular Contracture after Breast Augmentation: An Update for Clinical Practice", Arch Plast Surg, vol. 42, 2015, 532-543.

Keiler, Jonas, et al., "Neointimal fibrotic lead encapsulation—Clinical challenges and demands for implantable cardiac electronic devices", Journal of Cardiology, vol. 70, 2017, 7-17.

Kyle, Daniel J.T., et al., "Development and functional evaluation of biomimetic silicone surfaces with hierarchical micro/nano-topographical features demonstrates favourable in vitro foreign body response of breast-derived fibroblasts", Biomaterials, vol. 52, 2015, 88-102.

Nichols, Scott P., et al., "Biocompatible Materials for Continuous Glucose Monitoring Devices", Chem Rev., vol. 113, No. 4, 2013, 2528-2549.

Sedlacek, Marko, et al., "Use of Roughness Parameters Ssk and Sku to Control Friction—A Method for Designing Surface Texturing", Tribology Transactions, vol. 60, No. 2, 2017, 260-266.

Seewig, J., "Areal Filtering Methods. In: Leach R. (eds) Characterisation of Areal Surface Texture", Springer, Berlin, Heidelberg. https://doi-org.mu.idm.oclc.org/10.1007/978-3-642-36458-7_4, 2013, 1-355.

Sforza, Marcos, et al., "Preliminary 3-Year Evaluation of Experience With SilkSurface and VelvetSurface Motiva Silicone Breast Implants: A Single-Center Experience With 5813 Consecutive Breast Augmentation Cases", Aesthetic Surgery Journal, vol. 38, No. S2, 2018, S62-S73.

* cited by examiner

SURFACE TEXTURES OF MEDICAL DEVICES

CROSS-REFERENCE TO RELATED APPLICATIONS

This application claims priority to and the benefit of the filing of Netherlands Patent Application No. NL 2027599, filed on Feb. 19, 2021, titled "Biocompatible polymeric implant material having a textured surface". The specification and claims thereof are incorporated herein by reference.

BACKGROUND

Embodiments of the present are directed to medical devices having a textured surface.

Many medical devices such as implants for the human and animal body are known and frequently used to repair damage caused by an accident or by degeneration, to treat a disease, or for cosmetic reasons. Many of these implants are either in part or wholly made from polymeric materials, as opposed to metal or ceramic material. The implants may be required to remain in the body for a long or short period of time, but in either case, the use of polymeric materials that are biocompatible is required.

The human or animal body will react with an immune response to any medical implant, defined as the foreign body response (FBR). The foreign body response begins with protein deposition on the implant surface, is followed by inflammatory cell infiltration, and culminates in a thick fibrous capsule, principally composed of collagen surrounding the implant. Fibrous encapsulation of implants is therefore thought of as the end-result of an aberrant, undesirable immune response to the implant material. For certain medical implants, the formed fibrous capsule—also defined as implant fibrosis—may prevent the desired interaction between the implant surface and healthy, normal tissue. Since the inception of medical implants, the problem of fibrous tissue encapsulation due to the foreign body response has plagued long-term device functionality across most therapeutic areas. For example, subcutaneous continuous glucose sensors used by patients with diabetes must be replaced every 14 days because fibrous encapsulation of the sensor by the body prevents the sensors from properly detecting blood-glucose levels of the patient (DOI: 10.1021/cr300387j). Cardiac pacing leads implanted in patients with cardiac arrhythmia must routinely be replaced but are often not removed because fibrous encapsulation of the lead makes removal extremely risky for the patient (DOI: 10.1016/j.jjcc.2017.01.011). Breast implants can deform after the formation and contracture of a fibrous capsule, defined as capsular contracture (DOI: 10.5999/aps.2015.42.5.532), which requires surgical revision.

It has been shown in the literature that implant surface texture (also, surface structure, surface architecture, topography) may influence this foreign body response and can reduce the formation of fibrous tissue as well as prevent implant migration. However, the cellular mechanism driving these effects of surface texture are still largely unknown. Moreover, the specific type of surface texture—in terms of geometric scale, form of features, arrangement, regularity, etc—necessary to most desirably influence the foreign body response, is still not understood. Nor is it known if there is a universal surface structure that can be applied to various materials in scalable ways to reduce or positively influence the foreign body response to a variety of implant types and compositions.

In some foreign body response related maladies such as capsular contracture, microbial-produced biofilm and microbial adhesion to the implant surface has been associated with the etiology. It has also been shown in the literature that certain surface textures may reduce microbial adhesion and biofilm formation, although a precise characterization of the necessary surface structure parameters has not been elucidated.

Other strategies to reduce or positively influence the foreign body response such as coatings or drugs have been presented in the literature; however, these modifications require extensive changes to the medical implant design, material composition, and manufacturing process, which may make them unattractive strategies in practice. Alternatively, altering the surface texture of an implant in particular ways may provide a more efficient route to controlling the foreign body response.

There are many prior art publications directed to the surface texture of implant materials. A couple of recent examples follows here below.

WO2019/118983 describes laminated elastomeric articles comprising a first film laminated onto an elastomeric sheet. The first film has a certain surface roughness which is studied with a Keyence 3D scanning confocal microscope according to ISO 25178.

WO2018/213390 describes an implantable medical device with nanopatterned surface modifications which can mimic a natural environment and thereby reduce an immune foreign body response.

WO2016/185186 describes a metal object having a microrough surface comprising microscale protrusions. According to a preferred embodiment the rough surface of the metal object has an average roughness (Ra) of up to 3 μm.

US2013190699 describes an intravascular catheter having a surface profile to prevent biofilm formation. The patent document mentions polyurethane, polyethylene and silicones as possible biocompatible materials. No specific range of directive surface texture parameters such as developed interfacial ratio or peaks density are disclosed and are expectedly low for the disclosed surfaces. Furthermore, no methods enabling scaling to other polymer materials are provided.

US2010226943 describes articles with spaced features on the surface for non-toxic bio-adhesion control. The spaced features within a grouping being spaced apart at an average distance of about 1 nanometer to about 500 micrometers and each feature having a surface that is substantially parallel to a surface on a neighboring feature. The articles can be applied in biomedical applications and can be made of, for example organic polymers, thermoplastic polymers, thermoset polymers and biodegradable polymers. The features are highly ordered with highly aligned parallel groupings of features. Such alignment may be deleterious for capsular contracture because a high degree of fibrous tissue alignment oriented parallel with the implant surface is associated with high contractility of the capsule.

US20060219143 describes a surface coating for resisting or enhancing bio-adhesion. The surface coating comprises a polymer and has a pattern defined by a plurality of spaced apart features attached to or projected into a base surface. The features each have at least one microscale dimension and the spacing between adjacent features is between 0.5 and 5 micron. Features are organized in highly ordered, repeating units; however, the literature suggests that in certain instances, disordered arrangement of features may be more preferable for a given cell and tissue response (DOI: 10.1038/nmat2013).

U.S. Pat. No. 9,775,933 describes improved medical surfaces for a variety of medical purposes. The biocompatible surface has a unique tight microstructure that demonstrates enhanced cellular response in the body, particularly when placed in contact with blood and can be employed in a wide variety of implantable devices. The polymers used to prepare these surfaces preferably are fluoropolymers, like polytetrafluoroethylene (PTFE). The disclosed surface texture is a product of the given production process of PTFE coinciding with the specific material properties of PTFE itself. Whether this surface texture could be feasibly applied to other polymeric material surfaces for other purposes is not disclosed.

US2011257623 describes implantable medical devices having micro- and macro-porous surface layers that reduce the foreign body response. The surface layer is coated on the medical device like, for example, biosensors, breast implants, prosthesis, surgical mesh implants, catheters and neuromodulation leads. The surface coating has an open-cell structure with a macrotopography that is defined by a plurality of peaks and valleys. The coating can comprise various polymers or metals. Given the relatively large size of spherical pores created, average surface roughness values on the order of <5 micron are not expected or disclosed. Moreover, creating such a network of interconnected spherical pores requires extensive revision of the manufacturing process of embodying medical implants.

Similar to the above publication, US2015238306 describes a vascular graft comprising a blood-contacting layer formed of a textured microporous biomaterial. The blood-contacting layer reduces fibrotic capsular formation. The textured microporous surface layer comprises peaks and valleys with feature sizes ranging from 5 to 100 s of microns.

U.S. Pat. No. 10,532,131 describes osteoinductive calcium phosphates with a porosity comprising micropores in a size range of 0.1-1.50 micron. These calcium phosphates have better osteoinductive properties and this results in faster and more profound bone formation. No description of polymers with similar surface features are provided, nor is an expected functionality related to foreign body response disclosed.

US20200253738 describes an object, comprising a surface part provided with a regular pattern of protrusions defined by their height, distance and top surface area.

The surface topography is capable of modulating the morphology, proliferation, biochemical functioning, differentiation, attachment, migration, signaling, and/or cell death of a cell population by physical stimulation; i.e. the surface topography is capable of regulating the foreign body response. The objects can be made of a metal, polymeric, composite or ceramic material and is used during cell culture. The disclosed topography does not include pores and is highly ordered.

US20200268499 describes an implant material having an implant surface comprising a plurality of tissue-contacting members arranged in a regular or irregular two-dimensional array, each tissue-contacting member having a convex curved tissue-contacting surface. The implant material is used preferably in breast implants and the surface structure improves the foreign body response and therefore also the capsular contracture around the implant material. The disclosed surface is entirely composed of convex features and no reciprocating pores.

U.S. Pat. No. 10,595,979 describes an implant comprising a textured surface. The textured surface of the implants is based on the surface structure of acellular dermal matrix material. The surface texture is described as 'smooth' and has an influence on the foreign body response. The surface texture is irregular and is analyzed in detail according to ISO 25178-2 (2012) (col. 12, l. 30) via different methods. The textured surface described in this patent publication is used in breast implants that are marketed by Establishment Labs under the tradename Motiva®. The breast implants have a textured surface according to this patent publication and also corresponding to the academic publication from the same inventors (DOI: 10.1016/j.biomaterials.2015.02.003). The textured surface has the tradenames SilkSurface® and SmoothSilk™.

The SilkSurface® implants show less encapsulation compared with implants having a completely flat surface, however there is still a need for improvement.

BRIEF SUMMARY OF THE INVENTION

One embodiment of the present invention provides for a medical device having a textured surface with an arithmetical mean height value (Sa) below about 3.0 µm and a developed interfacial area ratio (Sdr) above about 1.0 and a density of peaks (Spd) above about $1 \times 10^6$ peaks/mm$^2$. The textured surface may further have a texture aspect ratio (Str) above about 0.6. Further still, the textured surface may have a maximum height value (Sz) below about 40 µm. The texted surface is a a biocompatible polymeric material. For example, the biocompatible polymeric material is a polyester, a polyurethane, an organosilicon, or a polyolefin. The medical device may be selected from a breast implant, a cardiac or cardiovascular implant, a surgical mesh, a neurostimulation lead, an ophthalmic implant, a urological implant, a film, or a biosensor. In one example, the textured surface is over the entire surface or on a portion of at least one surface. For example, the textured surface in on an outer surface of the medical device. For example, the outer surface of the medical device is designed to come into contact with tissue or cells within the biological environment in which the medical device is designed to be used. In one embodiment, the Sa value, the Sdr value and the Spd value are measured according to ISO 25178 using a Gaussian low pass S-filter with a nesting index value of at least about 0.25 µm.

Another embodiment provides for a process for preparing a medical device of claim 1, comprising the steps of providing a microstructured template wherein the microstructured template comprises a textured surface with an arithmetical mean height value (Sa) below about 3.0 µm and a developed interfacial area ratio (Sdr) above about 1.0 and a density of peaks (Spd) above about $1 \times 10^6$ peaks/mm$^2$. The microstructured template is covered with a biocompatible polymeric material that is a solid or a liquid. The biocompatible polymeric material is permitted to conform to the textural contours of the template using one or more of elevated temperature, pressure, or vacuum. When a liquid polymeric material is used, the liquid is processed to a solidify when in contact with the template. Processing includes allowing the liquid polymeric material to cool or crosslink or transition from the glass phase to the solid phase over time. A textured biocompatible polymeric material is separated from the microstructured template, for example when the liquid polymeric material transitions to a solid such that it can be separated from the template while maintaining the texture on the surface of the polymeric material. The process is not limited to biocompatible polymeric material as polymeric material other than biocompatible polymeric material can be texturized by the same process. The Sa value, the Sdr value, and the Spd value can be measured according to ISO 25178 using a Gaussian low pass S-filter with a nesting index value of at least about 0.25 µm.

Another embodiment provides for a microstructured template used for preparing a medical device is further described. The template may have a textured surface with an arithmetical mean height value (Sa) below about 3.0 µm and a developed interfacial area ratio (Sdr) above about 1.0 and a density of peaks (Spd) above about $1\times10^6$ peaks/mm$^2$. In one embodiment, the Sa value, the Sdr value, the Spd value are measured according to ISO 25178 using a Gaussian low pass S-filter with a nesting index value of at least about 0.25 µm. For example, the microstructured template textured surface has a texture aspect ratio (Str) above about 0.6a and/or the textured surface has a maximum height value (Sz) below about 40 µm. In one embodiment the template material is a sintered ceramic material for example, the sintered ceramic material is tricalcium phosphate (TCP).

Another embodiment of the present invention provides for a method of treating a mammal in need of treatment comprising implanting a medical device into the mammal for example the mammal can be a human. The medical device can be selected from a breast implant, a cardiac or cardiovascular implant, a surgical mesh, a neurostimulation lead, an ophthalmic implant, a urological implant, or a biosensor. The treatment can be for example cosmetic breast augmentation or reconstruction and for example the medical device is a breast implant. The medical device may include a biocompatible polymer. In one embodiment, the method provides that the medical device when in use as an implant provides for at least one of i) reducing a fibrous capsule density, reducing a fibrous capsule thickness, or iii) increasing a fibroblast viability on the medical device implant textured surface that is in contact with tissue as compared to a second medical device implant used under the same conditions and of the same dimensions with no textured surface or a textured surface selected from one of a) an arithmetical mean height value (Sa) above about 3.0 µm and a developed interfacial area ratio (Sdr) below about 1.0 and a density of peaks (Spd) below about $1\times10^6$ peaks/mm$^2$; b) a surface that has an arithmetical mean height value (Sa) above about 3.0 µm and a developed interfacial area ratio (Sdr) below about 1.0, or c) a surface that has an arithmetical mean height value (Sa) above about 3.0 µm and a density of peaks (Spd) below about $1\times10^6$ peaks/mm$^2$.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

Although it is known that textured surfaces on implants may in certain circumstances have a positive effect on the foreign body response, and thus on the formation of fibrous tissue and encapsulation, there is still a need to provide a more universal surface architecture that can be applied to a wide array of different polymer materials with superior potency to reduce or positively influence the foreign body response. Such a surface texture could be advantageously applied to other medical implant surfaces that also suffer from adverse foreign body response including but not limited to subcutaneous glucose sensors, cardiac devices, surgical meshes, neural stimulation leads and sensors, ophthalmic implants, urinary implants, and breast implants as well as other applications as described in more detail herein.

After extensive research the inventor has surprisingly discovered that the specific surface textures applied to a variety of biocompatible polymeric materials according to one embodiment of the present invention reduces the thickness of the fibrous layer around the implant material.

Another advantage is that a reduced capsular fibrous density is observed around the implant material.

A further advantage is that healthy fibroblast viability is promoted.

This has the effect that reduced capsular contracture around a medical device comprising the surface texture, which is an advantage because capsular contracture can lead to pain and discomfort and also to deformation of the structure of the device, for example a breast implant.

DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Embodiment of the present invention are further explained by the following figures and examples. The accompanying examples are exemplary and explanatory of nature and are not limiting the scope of the invention. To the person skilled in the art, it may be clear that many variants, being obvious or not, may be conceivable falling within the scope of protection, defined by the present claims. The accompanying drawings, which are incorporated into and form a part of the specification, illustrate one or more embodiments of the present invention and, together with the description, serve to explain the principles of an embodiment of the present invention. The drawings are only for the purpose of illustrating one or more embodiments of the invention and are not to be construed as limiting thereto. In the drawings:

DETAILED DESCRIPTION OF THE INVENTION

Figure 1:
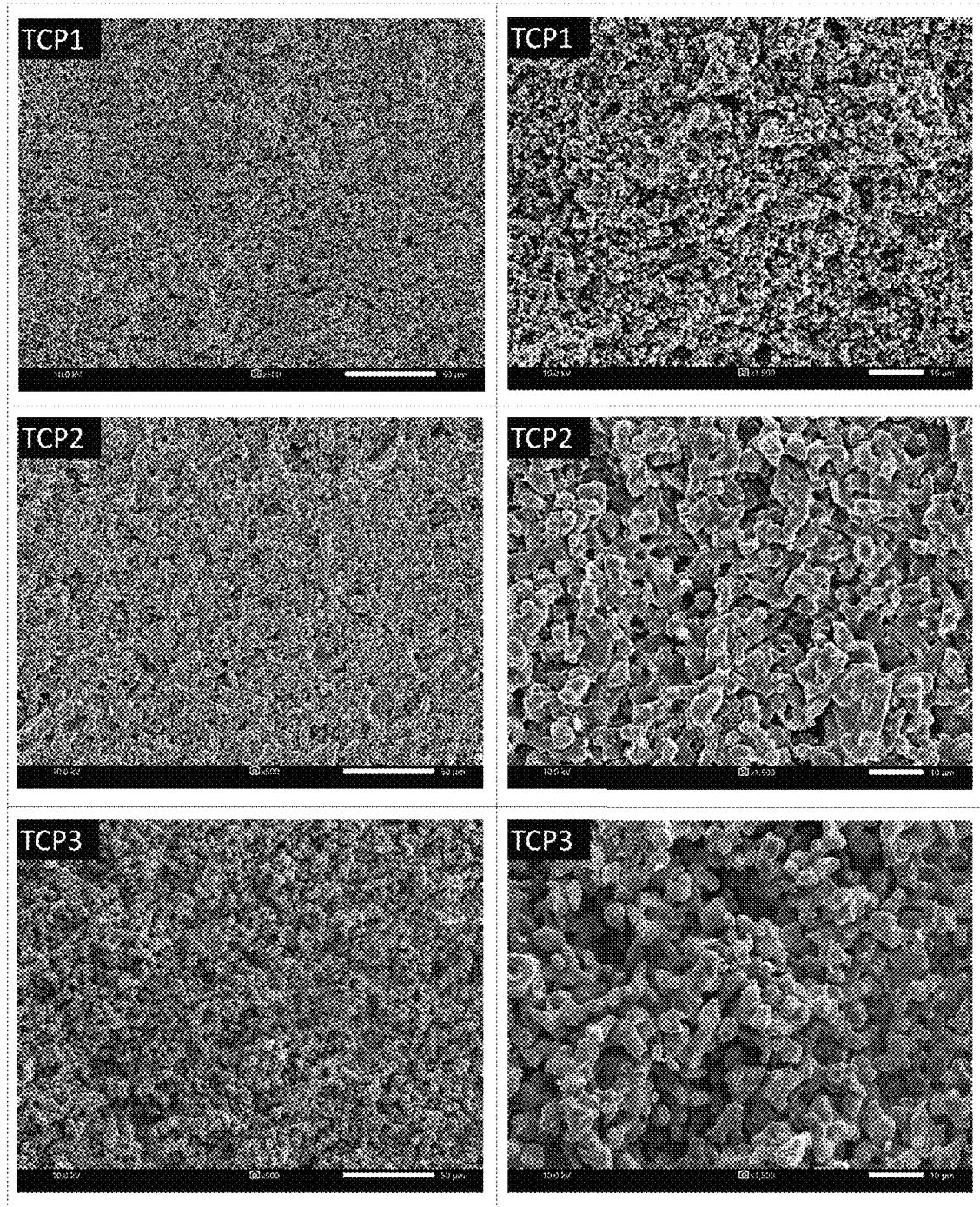
FIG. 1 shows scanning electron micrographs of the microstructured ceramic templates TCP1, TCP3 and TCP3 according to one embodiment of the present invention.

The articles "a" and "an" are used herein to refer to one or to more than one (i.e., to at least one) of the grammatical object of the article unless context clearly indicates otherwise. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

One embodiment of the present invention is directed to a biocompatible polymeric material, such as one incorporated in a medical device, having a textured surface with an arithmetical mean height value (Sa) below 3.0 μm and a developed interfacial area ratio (Sdr) above 1.0 and a density of peaks (Spd) above $1 \times 10^6$ peaks/mm$^2$, determined according to ISO 25178 using a Gaussian low pass S-filter with a nesting index value of 0.25 μm.

The biocompatible polymeric material according to one embodiment of the present invention can be a natural or a synthetic material. It can be a biodegradable or a permanent material. A biocompatible material is a material that has the ability to perform with an appropriate host response in a specific application. In particular, for a biocompatible polymeric material this is the ability of the material to perform its intended function, with the desired degree of incorporation in the host, without eliciting any undesirable local or systemic effects in that host. The biocompatible polymeric material can be a thermoplastic or a thermoset material. Examples of biocompatible polymeric materials are chitosan; cellulose, collagen, hyaluronic acid; PVC; polyolefins, like polypropylene (PP), polyethylene (PE), (ultra) high molecular weight polyethylene ((U)HMWPE) and polystyrene (PS); polymethylmethacrylate (PMMA); acrylonitrile butadiene styrene (ABS); polycarbonate (PC); polyesters, like polylactic acid (PLA); poly(lactic-glycolic) acid (PLGA); polyethylene terephthalate (PET) and polybutylene terephthalate (PBT); polyvinylalcohol (PVA); polyvinylpyrrolidone (PVP); polycaprolactone (PCL); polytetrafluoroethylene (PTFE); polyurethane (PU); polyamide (PA); polyethersulfone (PES); polyetheretherketone (PEEK); polyetherimide (PEI) and silicones. Combinations of these materials can also be used.

The biocompatible polymeric materials can comprise fillers, fibers and the usual polymer additives, like antioxidants and colorants. The biocompatible polymeric materials can also contain biologically active ingredients such as pharmacological agents, chemical agents, small molecules, proteins, growth factors, or other components that can elute from the material or remain bound to the material surface. These active ingredients can further elicit a desired biological response in combination with the surface texture.

Preferably, the biocompatible material is chosen from a polyester, a polyurethane, an organosilicon or a polyolefin.

The biocompatible polymeric material according to one embodiment of the present invention has a textured surface. This means that the surface embodies a complex shape made of a series of peaks and troughs (used interchangeably with "valleys") of varying heights, depths, and spacing. At least a portion of the surface of the biocompatible polymeric material directly in contact with the body, is not flat, but shows an average roughness below 10 μm. Within the specific field of use of breast implants, this roughness level is characterized as a smooth surface according to ISO14607 (2018).

The textured surface of the biocompatible polymeric material can be further defined by the use of the methods described in ISO 25178. According to ISO 25178 the surface roughness and shape can be determined using contact-type measuring instruments and non-contact type measuring instruments. As contact-type measuring instruments a surface roughness tester and atomic force microscope are mentioned and as non-contact type measuring instruments a white light interferometer and laser scanning microscope.

The textured surface of the biocompatible polymeric material according to one embodiment of the present invention has a surface with a texture in the micron and submicron range owing to textural features comprising both grains and pores (e.g. peaks and valleys) having dimensionality also on the micron and submicron range. Therefore, a laser microscope is chosen to determine the surface texture and other areal surface texture parameters. By using the laser microscope and dedicated software the surface texture of the biocompatible polymeric material according to one embodiment of the present invention can be characterized in detail by parameters as further explained in ISO 25178.

According to ISO 25178, the roughness of a surface area is determined. This is in contrast with earlier developed methods, like ISO 13565-1, wherein the roughness of a cross-sectional profile, a line on the surface, is determined. The ISO 25178 method therefore yields a more complete and detailed view on a textured surface.

More details and explanation about the surface texture parameters used in ISO 25178 can be found on the Keyence website: https://www.keyence.com/ss/products/microscope/roughness/surface/parameters.jsp and in The Area Field Parameters' by François Blateyron (DOI: 10.1007/978-3-642-36458-7_2). Here also the formulas for calculating the different parameters can be found.

The textured surface of the biocompatible polymeric material according to one embodiment of the present invention can be characterized by different parameters. These parameters are explained below:

The arithmetical mean height value (Sa) expresses, as an absolute value, the difference in height of each point compared to the arithmetical mean of the surface. This parameter is used generally to evaluate surface roughness.

The developed interfacial area ratio (Sdr) is expressed as the percentage of the definition area's additional surface area contributed by the texture as compared to the planar definition area. The Sdr of a completely level surface is 0. An Sdr value equal to 1 means that the measured surface possesses 100% more surface area compared to a perfectly flat surface. Thus, when a surface has any variable slope or textural features, its Sdr value becomes larger than 0.

The density of peaks (Spd) represents the number of peaks per unit area. A large number indicates more peaks in a certain area.

The autocorrelation length (Sal) represents the horizontal distance in the direction in which the auto-correlation function decays to the value[s] (0.2 by default) the fastest. Since Sal determines the distance at which the auto-correlation decreases the fastest, it can be used to determine whether there is a point at which the surface height changes abruptly The texture aspect ratio (Str) is a measure of uniformity and isotropy of the surface texture. The value is obtained by dividing the horizontal distance in the direction in which the auto-correlation function decays to the value[s] (0.2 by default) the fastest (equivalent to Sal) by the horizontal distance in the direction of the slowest decay of auto-correlation function to the value[s]. Str determines the ratio of distances at which the auto-correlation decreases the fastest and slowest, so it can be used to determine the presence of lay or orientation of texture.

The root mean square gradient (Sdq) can also describe the surface texture. Sdq is calculated as a root mean square of slopes at all points in the definition area. The Sdq of a completely level surface is 0. When a surface has any slope, its Sdq value becomes larger. Sdq can be used to differentiate surfaces with similar Sa but different feature spacing.

The maximum height value (Sz) is defined as the sum of the largest peak height value and the largest pit depth value within the defined area. The root mean square height (Sq), the skewness (Ssk) and the kurtosis (Sku) can further define the height distribution of features of the textured surface.

The textured surface according to embodiments of the present invention is characterized by an arithmetical mean height value (Sa) below 3.0 µm and a developed interfacial area ratio (Sdr) above 1.0. The Sa preferably is below 2.9 µm and more preferably below 2.8 µm. The Sa preferably is above 0.7 µm and more preferably above 0.8 µm. In certain embodiments Sa can, for example, be in a range of 0.1 to 10 µm or in a range of 0.3 to 5.0 µm.

The Sdr according to embodiments of the present invention preferably is above 1.05 and more preferably above 1.10. The Sdr preferably is below 20, more preferably below 15 and most preferably below 10. In certain embodiments Sdr can, for example, be in a range of 0.6 to 50 or in a range of 1.0 to 50.

Preferably, the textured surface according to embodiments of the present invention also comprises a density of peaks (Spd) above $1\times10^6$ peaks/mm$^2$. Preferably the density of peaks (Spd) is above $1.2\times10^6$ peaks/mm$^2$, more preferably above $1.4\times10^6$ peaks/mm$^2$, most preferably above $1.6\times10^6$ peaks/mm$^2$. Preferably, the density of peaks (Spd) is below $3.5\times10^6$ peaks/mm$^2$, more preferably below $3.2\times10^6$ peaks/mm$^2$, most preferably below $3.0\times10^6$ peaks/mm$^2$. In certain embodiments Spd can, for example, be in a range of $7.0\times10^5$ to $20\times10^6$ peaks/mm$^2$ or in a range of $1.0\times10^6$ to $20\times10^6$ peaks/mm$^2$.

The textured surface according to embodiments of the present invention can be further characterized by an autocorrelation length (Sal) above 3 µm, preferably above 4 µm, more preferably above 5 µm. The Sal preferably is below 25 µm, more preferably below 20 µm, most preferably below 15 µm. In certain embodiments Sal can, for example, be in a range between 1.0 to 25 µm or in a range of 2.0 to 20 µm.

The textured surface according to embodiments of the present invention can be further characterized by a texture aspect ratio (Str) above 0.6, preferably above 0.7, more preferably above 0.8. In certain embodiments Str can, for example, be in a range of 0.4 to 1.0 or in a range of 0.5 to 1.0.

The textured surface according to embodiments of the present invention can be further characterized by a maximum height value (Sz) below 40 µm, preferably below 35 µm, more preferably below 30 µm. The Sz preferably is above 8.0 µm, more preferably above 8.5 µm, most preferably above 9.0 µm. In certain embodiments Sz can, for example, be in a range of 0.1 to 60 µm or in a range of 0.5 to 50 µm.

The textured surface according to embodiments of the present invention preferably has a Sq above 0.5 µm, more preferably above 0.7 µm, most preferably above 1.0 µm. The Sq preferably is below 4.2 µm, more preferably below 4.0 µm, most preferably below 3.8 µm. In certain embodiments Sq can, for example, be in a range of 0.1 to 8.0 µm or in a range of 0.3 to 5.0 µm.

The textured surface according to embodiments of the present invention preferably has a Ssk below 0.00, more preferably below −0.05, most preferably below −0.10. In certain embodiments Ssk can, for example, be in a range of −3.0 to 3.0 or in a range of −1.0 to 1.0.

The textured surface according to embodiments of the present invention preferably has a Sku below 7.0, more preferably below 6.5, most preferably below 6.0. In certain embodiments Sku can, for example, be in a range of 2.0 to 5.0 or in a range of 3.0 to 5.0.

The textured surface according to embodiments of the present invention preferably has a Sdq above 0.1, more preferably above 0.2, most preferably above 0.3. The Sdq preferably is below 3.8, more preferably below 3.5, most preferably below 3.0. In certain embodiments Sdq can, for example, be in a range of 0.1 to 10 or in a range of 0.2 to 8.0.

The textured surface according to embodiments of the present invention preferably has a Spc above 5,000, more preferably above 10,000. The Spc preferably is below 150,000, more preferably below 100,000.

Embodiments of embodiments of the present invention have a surface texture that can be characterized by one to eleven of the textural parameters (Sa, Sdr, Spd, Sal, Str, Sz, Sq, Ssk, Sku, Sdq and Spc) as described above.

In an embodiment, the medical device comprising a biocompatible polymeric material with the textured surface is used in a mammal. The textured surface according to one embodiment of the present invention has the effect that the thickness of the fibrous layer around the biocompatible polymeric is reduced and also a reduction of the capsular fibrous density is observed around the biocompatible polymeric material. Without being bound to any specific biological mechanism, the textured surface promotes the healthy viability of fibroblasts and macrophages.

One embodiment of the present invention provides a process of preparing a biocompatible polymeric material having a textured surface for use in or as a medical device, wherein the process comprises the following steps:

1. Providing a microstructured template (for example a mandrel or mold) wherein the template has a surface texture comprising one or more of the following measurements: i) Sa (µm) of about 0.1 to about 10, or about 0.3 to about 5.0 or below about 3.0; ii) Sdr between about 0.6 to about 50; or about 1.0 to about 50 or above 1.0; iii) Spd (peaks/mm$^2$) of about $7 \times 10^5$ to about $20 \times 10^6$; or about $1 \times 10^6$ to about $20 \times 10^6$, or above $1 \times 10^6$ with no foreseen upper limit. Further still additional parameters such as one or more of the following may further define the textured surface: iv) Sz (µm): about 0.1 to about 60, most preferably about 0.5 to about 50; v) Str: 0.4-1.0; most preferably about 0.5 to about 1.0; vi) Sq: about 0.1 to about 8.0, most preferably about 0.3 to about 5.0; vii) Sdq: about 0.5 to about 10.0; most preferably about 1.0 to about 8.0; viii) Spc: about 5,000 to about 150,000; most preferably about 10,000 to about 100,000; ix) Sal (µm): about 1.0 to about 25.0; most preferably about 2.0 to about 20.0; x) Ssk: about −3.0 to about 3.0; most preferably about −1.0 to about 1.0; xi) Sku: about 2.0 to about 5.0; most preferably about 3.0 to about 5.0. In one embodiment, these features are measured or determined according to ISO 25178 using a Gaussian low pass S-filter with a nesting index value of at least 0.25 µm;
2. Covering the textured template surface with a biocompatible polymeric material. The polymeric material is applied to the textured template surface as either a solid or as a liquid polymeric mixture;
3. Conforming the biocompatible polymeric material to the contours of the textured template surface, using one or more of elevated temperature, pressure, or vacuum,
4. Solidifying the biocompatible polymeric material, and
5. Separating the biocompatible polymeric material and the microstructured template to form a texturized biocompatible polymeric material. For example, the biocompatible polymeric material is a medical device.

In one embodiment of the present invention, a medical device comprising a biocompatible polymeric material has a surface texture according to one or more of the following measurements: i) Sa (µm) of about 0.1 to about 10, or about 0.3 to about 5.0 or below about 3.0; ii) Sdr between about 0.6 to about 50; or about 1.0 to about 50 or above 1.0; iii) Spd (peaks/mm$^2$) of about $7 \times 10^5$ to about $20 \times 10^6$; or about $1 \times 10^6$ to about $20 \times 10^6$, or above $1 \times 10^6$ with no foreseen upper limit. Further still additional parameters such as one or more of the following may further define the textured surface: iv) Sz (µm): about 0.1 to about 60, most preferably about 0.5 to about 50; v) Str: 0.4-1.0; most preferably about 0.5 to about 1.0; vi) Sq: about 0.1 to about 8.0, most preferably about 0.3 to about 5.0; vii) Sdq: about 0.5 to about 10.0; most preferably about 1.0 to about 8.0; viii) Spc: about 5,000 to about 150,000; most preferably about 10,000 to about 100,000; ix) Sal (µm): about 1.0 to about 25.0; most preferably about 2.0 to about 20.0; x) Ssk: about −3.0 to about 3.0; most preferably about −1.0 to about 1.0; xi) Sku: about 2.0 to about 5.0; most preferably about 3.0 to about 5.0. In one embodiment, these features are measured or determined according to ISO 25178 using a Gaussian low pass S-filter with a nesting index value of at least 0.25 µm.

Preferably, a medical device composed of a biocompatible polymeric material has a textured surface comprising an arithmetical mean height value (Sa) below about 3.0 µm and a developed interfacial area ratio (Sdr) above about 1.0 and a density of peaks (Spd) above about $1 \times 10^6$ peaks/mm$^2$. In certain embodiments, the textured surface of the polymeric material also has a texture aspect ratio (Str) above about 0.6 and/or the textured surface has a maximum height value (Sz) below about 40 µm.

There are various processes by which a biocompatible polymeric material with a textured surface can be obtained.

In an embodiment, the first step in the process is to provide a microstructured template. The template can be used to directly transfer the microstructure to the biocompatible polymeric material. In this way the obtained polymeric material has a surface structure that is the inverse of the surface texture of the template.

A microstructured template may include both the positive and the negative form of microstructured surface features making up its surface texture, of which texture constitutes all or a portion of the template surface. In this way, a single template may transfer either or both the positive and negative form of the surface texture to a surface of another material over all or just a portion of a surface of another material, for instance a biocompatible polymeric material such as one incorporated into a medical device.

As used herein, 'template' is written in the described process and can be replaced by 'mold'. Template and mold are interchangeable.

The microstructured template can, for example, be made from a ceramic material, a metallic material, or a polymeric material. A microstructured template of the current invention can be obtained in various ways. For example, a template can be obtained by common additive manufacturing techniques, like, for example sintering and selective laser melting.

Also, lithography methods can be used to create a microstructured template. Lithography can be used to create templates from silicon, germanium, TCP, other ceramics, polymers, and metals. Lithography methods that can be used are, for example, photo lithography or UV lithography; electron beam lithography and grayscale lithography; and soft lithography.

A sequential combination of sintering and soft lithography is a preferred method by which a microstructured template can be created.

In a preferred embodiment, a microstructured template made up of ceramic material can be created according to a method described in the art (DOI: 10.22203/ecm.v027a20). The method is summarized by the following description; calcium phosphate powders are synthesized by mixing calcium hydroxide and phosphoric acid at a Ca/P molar ratio of 1.50. Grain size differences in the final ceramics are produced by carefully controlling the component reaction rates of the ceramic powder. The powders are mixed with diluted hydrogen peroxide and dried at room temperature to get microporous green bodies. The dry green bodies are subsequently sintered at temperatures ranging from 900-1200° C. for 8 h to achieve variable microstructures ranging from relatively small (e.g., <1 μm) at lower temperatures to relatively large (e.g., >1 μm) at higher temperatures. The resulting microstructured ceramic produced by sintering possesses surface grains and pores ranging from the micron scale to the submicron scale.

In one embodiment of the present invention, a microstructured template made up of a polymer can be prepared. For example, a flowable, low viscosity polymer such as silicone elastomer (e.g., Sylgard 184, Dow Corning), natural rubber (ZA22, Zhermack), or perflouropolyether (FluoroLink, Solvay) can be used to create a microstructured template. The flowable polymer fluid is poured over a pre-prepared microstructured template possessing a textured surface, for instance a microstructured ceramic as prepared above. The polymer fluid is allowed to seep into the contours of the textured surface of the microstructured template by the force of gravity, or with the addition of pressure and/or vacuum. The polymer fluid is solidified via chemical crosslinking at room temperature, elevated temperature, or using UV light, thus creating a solidified polymer film or slab on top of the textured template surface. The solidified polymer material is peeled away from the textured template surface, thereby producing a polymer material having a textured surface on a surface of the polymer material that conformed to the textured surface of the template. The textured surface of the polymer material is the inverse replicated surface texture of the textured template surface.

Figure 14:
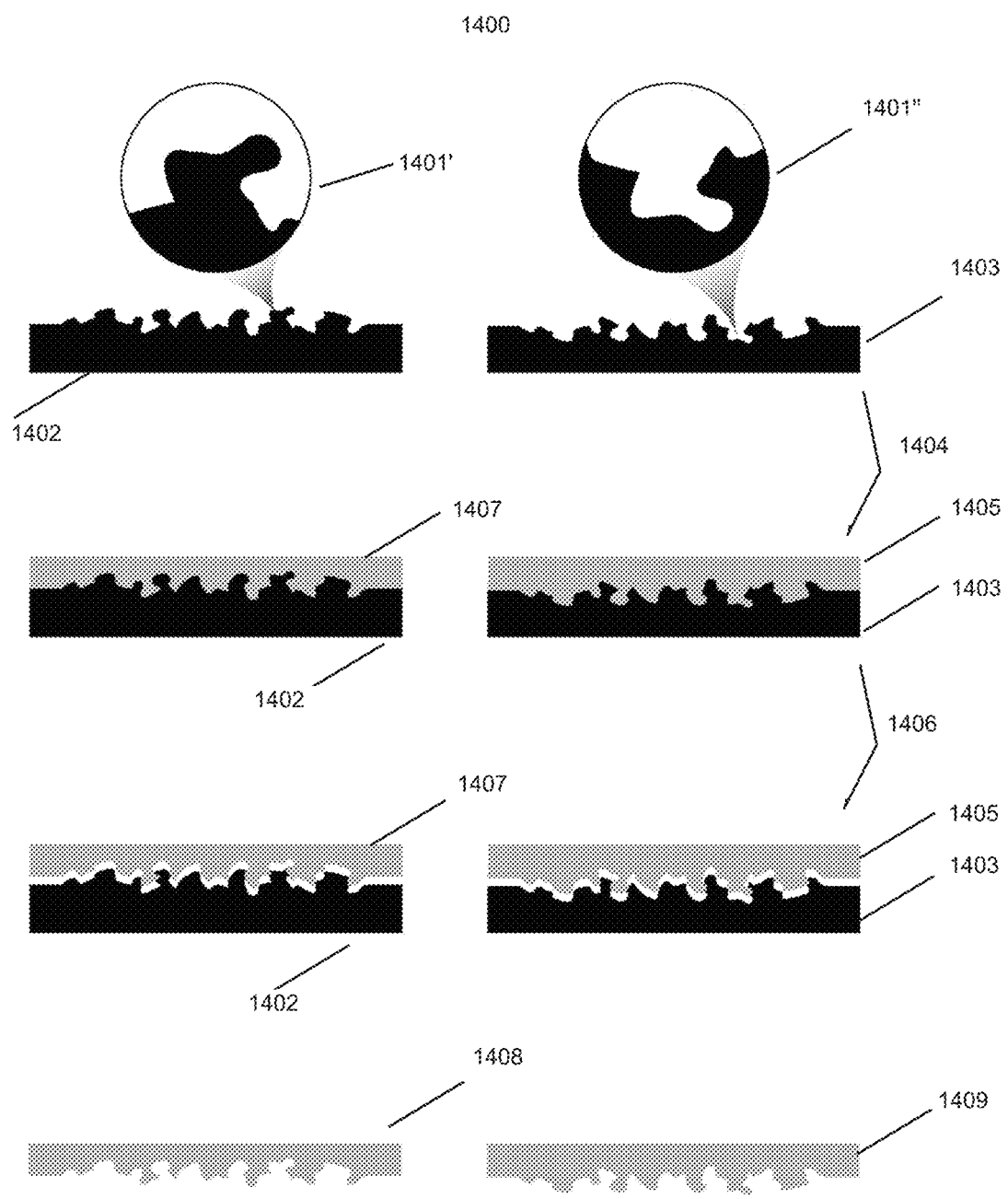
FIG. 14 illustrates a process for forming a textured polymeric material according to one embodiment of the present invention.

In another preferred embodiment, a microstructured template is created by electroforming (also, Galvano forming). Electroforming is a well-known method in the art for replicating nano- and microstructures. In this exemplary embodiment, a microstructured ceramic material is used as microstructured template substrate having the positive form of a textured surface to be replicated. The microstructured ceramic template is sputter coated with a thin layer (e.g., <20 nm) of nickel vanadium using plasma vapor deposition. The sputter coated template is then mounted in a electroforming bath, typically consisting of boric acid and nickel chloride. A negative voltage is applied to the coated template which causes the nickel ions to condense atom by atom on the surface of the exposed template. Over time, the template surface is deposited with a nickel layer, built up atom by atom on the surface of the template to a total thickness of 300-500 μm. The template and resulting electroformed nickel layer, referred to as a shim, is removed from the electroforming batch and the nickel shim is mechanically detached from the microstructured template surface. To further detach template debris from the electroformed nickel shim, ultrasonication in a weak acid may be applied. The electroformed nickel shim is cleaned and dried. The electroformed nickel shim possesses a surface texture replicating with high fidelity the inverse form of the textured template surface. The obtained electroformed nickel shim with textured surface can be used as a template for production of polymeric materials having textured surfaces with equivalent and inverse form of the textured nickel mold surface via a process as illustrated in FIG. 14. The advantage of this template preparation method is a robust, scalable way of producing microstructured templates that can be readily applied in large-scale manufacturing processes to obtain a textured polymeric material such as one making up a medical device. Preferred large-scale manufacturing processes include nanoimprinting, roll embossing (roll-to-roll and roll-to-plate), hot embossing, dip coating, spray coating, and injection molding.

In a preferred embodiment of the present invention, the template material has a textured surface that is replicated with good fidelity in the surface of the biocompatible polymeric material which is then used to form a medical device or implant according to an embodiment of the present invention. The surface parameters of the template material are comparable with the surface parameters of the biocompatible polymeric implant material. Preferably, the template material has a textured surface with an arithmetical mean height value (Sa) below about 3.0 μm and a developed interfacial area ratio (Sdr) above about 1.0. Preferably, the textured surface of the template material has a density of peaks (Spd) above about $1 \times 10^6$ peaks/mm². Preferably, the textured surface of the template material also has a texture aspect ratio (Str) above 0.6 and/or the textured surface has a maximum height value (Sz) below 40 μm.

When ceramic material is used as a template material, the ceramic material preferably is tricalcium phosphate (TCP), hydroxyapatite, aluminum oxide (alumina), zirconium oxide (zirconia), titanium oxide, more preferably tricalcium phosphate. Tricalcium phosphate can be alpha or beta tricalcium phosphate, preferably, beta tricalcium phosphate.

The ceramic material can contain fibers such as alumina, mullite, silicon carbide (SiC), zirconia or carbon. Fiber-reinforced ceramics do not have the major disadvantages of conventional ceramics, namely brittleness and low fracture toughness, and limited thermal shock resistance. In this respect, ceramic materials can be made in large volumes and can be machined without cracking, e.g. for template production via machining methods known in the art.

According to a second step, the template material is covered with a biocompatible polymeric material as a solid or as a liquid for the purpose of replicating the template surface texture onto a surface of the biocompatible polymeric material such as one incorporated into a medical device. When this procedure is followed the resulting biocompatible polymeric material has a surface texture that is the inverse replicated form of the template surface texture.

A liquid polymeric mixture is for example a solution or mixture comprising a polymer dissolved in one or more solvents; or for example, a mixture of a polymer base component with a polymer catalyst component; or for example, a mixture of a polymer base component with a curing agent component; or for example, any combination of these examples. The terms "liquid polymeric material", "polymeric mixture", and "polymeric solution" can all be used interchangeably throughout this disclosure.

In a third step, the biocompatible polymeric material is conformed to the textural contours of the template or mold using, in combination or separately, elevated temperature, pressure, or vacuum. For thermoplastic polymer materials it is possible to bring the polymeric material above the glass transition temperature and cover the template or mold material with the molten thermoplastic polymer material to create intimate contact between the template material and the molten thermoplastic material. In a preferred embodiment pressure or vacuum is applied to drive the molten thermoplastic material into the contours of the textured template surface. In this way, the inverse form of the textured template surface is transferred onto a surface of the thermoplastic material and replicated with good fidelity.

For thermoset polymeric materials the surface of the textured template is covered with the thermoset polymeric material in the form of a liquid at room temperature. The liquid polymeric mixture flows into the contours of the textured template surface provided the viscosity of the mixture is suitably low. The monomers and the other components in the liquid polymeric mixture react and solidify to form the thermoset polymeric material. The solidification of the liquid polymeric mixture may occur at about room temperature or at elevated temperature depending on the nature of the polymer, for example room temperature silicone rubber and high temperature silicone rubber. Alternatively, a UV-curable polymer can be used in place of the thermoset polymeric material, for example perfluoropolyether. In this case, UV light is applied to polymerize and solidify the liquid polymeric mixture while it is in direct contact with the textured template surface. During solidification, the inverse form of the surface texture of the template material is transferred to the surface of the polymeric material in direct contact with the template. Elevated pressure or vacuum facilitate the reliable transfer of the texture.

In an embodiment, a resorbable synthetic or resorbable natural polymer is used in place of a thermoset polymeric material. Preferred synthetic resorbable polymers include polycaprolactone, polyethylene glycol, polyurethane, polydioxanone, polymethyl methacrylate, polyglycolic acid/polyglycolide, polylactic acid/polylactide, polylactic-co-glycolic acid, polyhydroxybutyrate, polycyanoacrylates, and polyvinylpyrrolidone. Preferred natural resorbable polymers include: cellulose, chitin, collagen, chitosan, gelatin, carrageenan, hyaluronic acid, xanthan gum, acacia gum, fibrin, and alginate. A resorbable polymer is dissolved in a suitable solvent to create a liquid polymerizable mixture of a suitably low viscosity, for instance less than 4,000 mPa·s. The microstructured template is covered with the liquid polymerizable mixture and optionally pressure or vacuum is applied to force the mixture into the contours of the textured template surface. Elevated temperature is applied to evaporate the solvent, thereby solidifying the polymer. In this way, the inverse form of the textured template surface is transferred onto a surface of a resorbable polymer and replicated with good fidelity.

In general, elevated pressure or vacuum improve the fidelity of replication from the surface texture of the textured template surface to a surface of a polymeric material. In an embodiment, pressure is applied to a flowable polymer in direct contact with a textured template surface using centrifugal force. A centrifuge can easily apply pressures many times the force of gravity while having a self-leveling effect of the polymeric material on top of the template surface thereby producing a uniform polymer thickness or depending on the application a polymer with variable thickness. Other preferred methods for applying pressure include using a heated press and piston to drive a flowable polymeric material into the contours of the textured template surface.

When the thermoplastic polymeric material is cooled to below the glass transition temperature it solidifies. After solidification it can be removed from the surface of the template material by peeling. The resulting polymeric material possesses a textured surface equivalent to the inverse of the textured surface of the template; this texture is present on the surface of the polymeric material that was in direct contact with the template.

When solidification of the thermoset material has been completed the thermoset polymeric material can be removed from the surface of the template by, for instance, peeling. If elevated temperature was applied to cure the polymer, it is preferable to let the polymer cool down to room temperature prior to removal from the template surface. The resulting polymeric material possesses a textured surface equivalent to the inverse of the textured surface of the template; this texture is present on the surface of the polymeric material that was in direct contact with the template.

When a ceramic material is used as the template material, for example TCP, the ceramic material can be dissolved in a strong acid to aid in the removal of the textured polymeric material. During dissolving ultrasonication can be applied.

When a harder template material is used, e.g. metal, the textured polymeric material can be removed from the surface of the metal template by the use of a demolding release agent. Preferred release agents lower the surface energy of the template material, thereby reducing the force required to peel the textured polymer away from the template surface. Such preferred release agents can be applied to the template surface in the form of a thin surface coating via various ways such as vapor deposition or sputter coating. Preferred release agents are biocompatible and medical grade. Preferred release agents include fluoropolymers such as polytetrafluoroethylene, akylphosphonic acids such as n-octylphosphonic acid, and carbon.

According to a third method it is possible to make a digital scan of the surface of a ceramic template material, using for example nano-CT or atomic force microscopy, to produce a 3-D digital reconstruction of template surface. Such a digital 3-D scan can be used as input for lithographic creation of the template or mold microstructure in various other materials and form factors. Alternatively, such a digital 3-D scan could be used to fabricate the desired surface texture directly on the biomaterial surface without the need for a physical template or mold, using for example maskless lithography or 2 photon polymerization techniques.

One embodiment of the present invention is also directed to a microstructured template for use in the process for the preparation of the biocompatible polymeric material, wherein the template has a textured surface according to one or more of the following measurements: i) Sa (µm) of about 0.1 to about 10, or about 0.3 to about 5.0 or below about 3.0; ii) Sdr between about 0.6 to about 50; or about 1.0 to about 50 or above 1.0; iii) Spd (peaks/mm$^2$) of about $7 \times 10^5$ to about $20 \times 10^6$; or about $1 \times 10^6$ to about $20 \times 10^6$, or above $1 \times 10^6$ with no foreseen upper limit. Further still additional parameters such as one or more of the following may further define the textured surface: iv) Sz (µm): about 0.1 to about 60, most preferably about 0.5 to about 50; v) Str: 0.4-1.0; most preferably about 0.5 to about 1.0; vi) Sq: about 0.1 to about 8.0, most preferably about 0.3 to about 5.0; vii) Sdq: about 0.5 to about 10.0; most preferably about 1.0 to about 8.0; viii) Spc: about 5,000 to about 150,000; most preferably about 10,000 to about 100,000; ix) Sal (µm): about 1.0 to about 25.0; most preferably about 2.0 to about 20.0; x) Ssk: about −3.0 to about 3.0; most preferably about −1.0 to about 1.0; xi) Sku: about 2.0 to about 5.0; most preferably about 3.0 to about 5.0. In one embodiment, these features are measured or determined according to ISO 25178 using a Gaussian low pass S-filter with a nesting index value of at least 0.25 μm.

In a preferred embodiment of the present invention, a microstructured template for use in the process for the preparation of the biocompatible polymeric material has a textured surface with an arithmetical mean height value (Sa) below 3.0 μm, a developed interfacial area ratio (Sdr) above 1.0 and a density of peaks (Spd) above $1\times10^6$ peaks/mm$^2$, determined according to ISO 25178 using a Gaussian low pass S-filter with a nesting index of 0.25 μm. The microstructured template can be used in the process for the preparation of the biocompatible polymeric material. Preferably, the template has a texture aspect ratio (Str) above 0.6 and/or a maximum height value (Sz) below 40 μm.

Referring now to FIG. 14, a process is illustrated 1400 to from a texturized biocompatible polymeric material from a microstructured template with positive features 1402 or negative features 1403 is illustrated. It should be noted that the template with negative features 1403 represents the voids of the template with positive features 1402. The features of the template are illustrate for example at 1401' (peaks) and 1401" (valleys). Therefore, a template may possess the positive or negative form of microstructured features making up its surface texture, of which the surface texture constitutes all or a portion of the template surface. According to the process disclosed, a template can be used to directly transfer the inverse form of its surface texture to a surface of another material, for instance a biocompatible polymeric material 1405 or 1407 which may be used in the formation of a medical device. The polymeric material 1407 or 1405 is applied to a respective template 1402 or 1403. The biocompatible polymeric material conforms to the textured template contours with or without the assistance of one or more of elevated temperature, pressure or vacuum when the polymeric material is applied as a liquid or solid. After the conforming step 1404, the polymeric material is separated from the template at step 1406 as is shown in the void between the textured template surface and the textured surface of the polymeric material. The resulting texturized polymeric material 1408 or 1409 represents a textured surface that is the inverse of the texturized surface of the template. The resulting texturized polymeric surface 1408 or 1409 has a surface texture on a portion or all of at least one of its surfaces that is the inverse replicated form of the template surface texture. In this way, the template is applied as a mold to conform a material to the contours of the surface texture of the textured template surface, leaving an imprinted replication of the inverse form of the template surface texture on a material surface. The words 'template' and 'mold' are thus used interchangeably throughout this disclosure.

Figure 15:
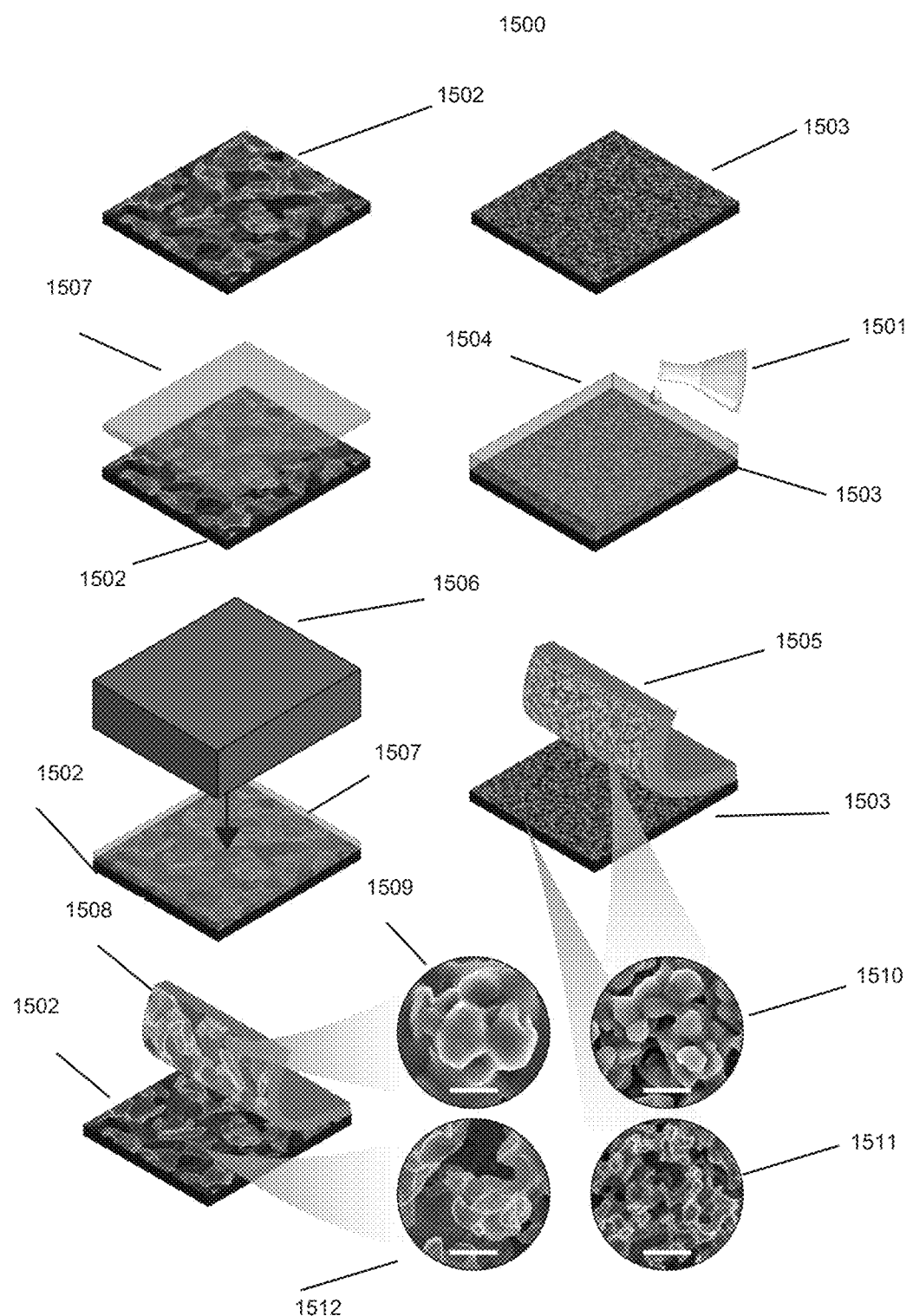
FIG. 15 illustrates a process for forming a textured polymeric material according to one embodiment of the present invention.

Referring now to FIG. 15, another embodiment of the present invention is provided for forming the textured polymeric material 1500. A template 1503 is covered with a polymeric material in the form of a liquid polymeric mixture 1504 poured from 1501. A liquid polymeric mixture 1501 is flowed onto a textured template 1503. The addition of one or more volatile solvents to a liquid polymeric mixture also may improve the fidelity of surface texture replication from the textured template surface to the polymeric material surface by lowering the viscosity and resistance to flow. The liquid polymeric mixture is allowed to solidify on the textured template surface in the presence or absence of pressure such as centrifugation or vacuum, after which the solidified texturized polymeric material 1505 can be separated from the template 1503, by for instance peeling it away from the template.

In another embodiment, a template 1502 is covered with a solid polymeric material 1507, preferably a thermoplastic material. The polymeric material conforms to the template structure with or without the aid of the application of heat, pressure, vacuum. To improve replication fidelity, a piston or platen 1506 provides direct pressure onto the surface of the polymeric material 1507 that is in contact with the textured template surface wherein pressure is applied in the direction of the arrow as shown. Preferably, pressure is applied while the polymeric material is heated above its glass transition temperature to ensure it can flow into the contours of the textured template surface. During the course of applying pressure, for instance using a piston or platen, an additional texture is added to a surface of the polymeric material (e.g. thermoplastic material), for example by applying another textured template surface to the side of the piston or platen coming into direct contact with the polymeric material. In other embodiments, it may be preferred to prevent this effect, by providing a piston or platen with a smooth contact surface. The polymeric material is solidified, by for example, in the case of a thermoplastic polymer, cooling it to below its glass transition temperature while on the surface of the template 1502. After solidification, the solidified polymeric material 1508 can be removed from the surface of the template 1502 by, for instance, peeling it away from the template.

The resulting surface features of the textured polymeric material are illustrated in SEM micrographs 1509 and 1510, specifically a medical grade silicone material. The features from the textured template surface are illustrated in SEM micrographs 1512 and 1511, specifically microstructured nickel shims. The resulting polymeric materials possess surface textures 1509 and 1510 equivalent to the inverse of surface textures 1512 and 1511 of the templates; this texture is present on the surface of the polymeric material that was in direct contact with the template. The scalebar in all SEM micrographs is 5 μm.

One embodiment of the present invention is further directed to the use of the biocompatible polymeric material for at least part of the surface of a medical device. The medical device is preferably for a mammal, more preferably a human.

One embodiment of the present invention is also directed to a medical device fora mammal comprising the biocompatible polymeric material having a textured surface according to an invention embodiment.

The invention is also directed to a medical device comprising the biocompatible polymeric implant material having a textured surface according to the invention. Preferably, the entire surface of the medical implant comprises a biocompatible polymeric implant material having a textured surface. More preferably, the textured surface is on an outer surface of the medical device.

The medical device can be any implant that can be used in a mammal. Medical implants are devices or tissues that are placed inside or on the surface of the body. Many implants are prosthetics, intended to replace missing body parts. Other implants deliver medication, monitor body functions, or provide support to organs and tissues. Medical implants can be made from metal, plastic, ceramic or other materials including natural materials.

Medical implants can be placed permanently or they can be removed once they are no longer needed. For example, stents or hip implants are intended to be permanent. But chemotherapy ports or screws to repair broken bones can be removed when they no longer needed. Examples of medical implants are cochlear implants, breast implants, hip implants, cardiac implant, surgical meshes, stents, (bio) sensors, intraocular lenses and birth control devices.

Preferably, in view of an embodiment of the present invention and the problem it solves, the implant is a breast implant, a cardiac or cardiovascular implant, a surgical mesh, a neurostimulation lead, an ophthalmic implant, a urinary implant, or a biosensor. More preferably, the implant is a breast implant fora human.

In one embodiment of the present invention, a medical device as defined herein may come in contact with biological systems such as biological fluid, tissue, and cells, whether vital or nonvital, in vitro or in vivo. Contact of the medical device with biological systems may be permanent, as in the example case of a heart valve which when in use in the body is not intended to be removed, or temporary as in the case of a urinary catheter.

Medical devices as used herein include biomedical implants and prostheses for both hard and soft tissue, including breast implants, heart valves, vascular and urological stents, ocular implants, artificial joints, and films for example drug delivery films but not limited thereto.

Medical devices as defined herein may also include urological catheters, central venous catheters, endotracheal tubes, and others which may be inserted into bodily orifices rather than surgically implanted.

The textured surfaces described herein may possess additional functionality in reducing biological adhesion of cells, viruses, bacteria and/or biofilm and/or the proliferation thereof on the textured surface of the medical device when the medical device is exposed to an environment in which the cells, bacteria or biofilm exist.

In another embodiment, medical device is a film applied to a surface to resist pathogen transmission, such as biological fluid, tissue, cells, bacteria or viruses. Such medical device can also include biomedical packaging containing biomedical equipment, tools, or other products. In another embodiment, medical device is a film applied to highly contacted hospital surfaces such as door handles, furniture, desks, computers, keyboards, and the like. Film can be replaced between surgeries to prevent infection. In an alternative embodiment, a film can be applied to clean room surfaces, for instance in the biomedical industry. Film can be applied in food packaging, to deter pathogen adhesion and proliferation. Film can also be applied elsewhere in the food industry including surfaces inside food processing plants. Film can be applied in the toy industry, such as for children's toys. Film can be applied in the transportation industry, such as on surfaces on and inside public transit, such as buses, trams, and trains. Film can be applied to consumer electronics such as the surface of cell phones, keyboards, touch screens, and mouses.

Medical devices as defined here may incorporate the disclosed textures on all or part of the surfaces of the medical device. For example the described textured surface may be on a surface of medical device the is proximal (nearest) the patient while the described textured surface is not on the surface that is distal to the patient for example in the case of a biosensor placed onto the skin surface. The texturized surfaces may be on the inside and/or an outside of the medical device, depending on the specific function of the device and where the medical devices comes in contact with biological systems. In one embodiment, the medical device is formed from a polymer sheet having a textured surface, the textured surface includes one or more areas comprising an arithmetical mean height value (Sa) below 3.0 µm, a developed interfacial area ratio (Sdr) above 1.0, a density of peaks (Spd) above $1\times10^6$ peaks/mm² as determined according to ISO 25178 using a Gaussian low pass S-filter with a nesting index of 0.25 µm. For example, a medical device such as a film may be exposed to the environment of a biological system on both sides of the film which first side may be described as top side and a second side may be described as a bottom side of the film. In another example, the medical device may be a breast implant having a polymer shell with a top side of the polymer designed to be exposed to the environment of the biological system on an exterior side of the implant and the second side (equivalent to a bottom side of the film) of the implant is designed to be on an interior side of the implant which is not exposed to the biological environment but instead exposed to the interior portion of the implant shell.

Medical devices as defined herein, when in use, may be fully encapsulated by or within the biological system or only in contact with the biological system on one side of the medical device. In one embodiment a medical device can be applied externally or internally to a living organism. For example, a medical device that is a sensor/biosensor can be fully or partially implanted in the subcutaneous space or a sensor can be adhered on the skin without penetrating the skin. In another embodiment, the medical device having a textured surface may include plasters applied to superficial wounds or granuloma repair prevention of granuloma formation for skin wounds or granuloma repair prevention of granuloma formation for skin wounds.

Medical devices as defined herein also include medical instruments that come in contact with biological systems such as endotracheal tubes, stethoscopes, and stents.

Examples of medical devices, medical implants and medical instruments are contact lens; components and surfaces of dialysis management devices such as, for example, a dialysis line; components and surfaces of urinary management devices such as, for example, a urinary catheter; components and surfaces of central venous devices such as, for example, a urinary catheter; surfaces of implanted devices such as, for example, pacemakers, artificial pancreas, and the like; ports on catheters such as, for example, feeding tube ports, implanted venous access ports; bone implants, such as, for example, an orthopedic implant or other implant in a hip joint replacement or repair, knee replacement or repair, shoulder replacement or repair, elbow replacement or repair, and an ankle replacement or repair; implantable and extracorporeal drug delivery systems and cell encapsulation devices; soft tissue repair meshes, and tissue grafts.

For clarity, medical devices as defined herein do not include syringe stoppers, seals, or containers used to contain drugs which do not come in direct contact with biological systems.

The textures disclosed herein may exert additional biological functionalities beyond limiting fibrosis and the foreign body response. Examples of these functionalities include resisting bacterial and viral adhesion and proliferation, and resisting blood coagulation and thrombosis. Other functionalities include enhancing biological adhesion and integration of biological tissue such as bone and soft tissue. Additional functionalities include guiding cell differentiation, instructing cell migration, promoting cell survival, and enhancing or perpetuating a certain cellular phenotype. It is known in the literature that in general, surface topographies may have a broad and variable effect on biological systems and processes. These effects may be static, dynamic, acute, chronic, temporal, or permanent. These textures may also enhance the lubricity of medical devices by reducing frictional forces of the textured surface.

EXAMPLES

1: Fabrication and Characterization of Functional Surface Architectures

Example 1.A—Sample Fabrication

Microporous ceramic template materials were prepared according to methods previously described in the literature (DOI: 10.22203/eCM.v027a20). Briefly, calcium phosphate powders were synthesized by mixing calcium hydroxide and phosphoric acid (both from Fluka/Sigma-Aldrich, St. Louis, MO, USA) at a Ca/P molar ratio of 1.50. Grain size differences in the final ceramics were produced by carefully controlling the component reaction rates of the ceramic powder. The powders were mixed with diluted hydrogen peroxide (0.1%) (Merck, Darmstadt, Germany) and dried at room temperature to get microporous green bodies. The dry green bodies were subsequently sintered at temperatures ranging from 900-1,200° C. for 8 h to achieve variable microstructures ranging from relatively small at lower temperatures to relatively large at higher temperatures. Microporous discs (9 mm diameter×1 mm thickness) were machined from the ceramic bodies using a lathe and a diamond-coated saw microtome (Leica SP1600; Leica, Solms, Germany), then ultrasonically cleaned in deionized water and ethanol.

Molds of the desired template surface architecture were prepared using a soft-lithography PDMS casting approach. PDMS (Sylgard® 184; Dow Corning) was prepared at a ratio of 10:1 (w/w) base to curing agent, degassed under vacuum, then poured over the template ceramic discs. Cast PDMS was further degassed under vacuum to fully impregnate the template architecture with PDMS. The PDMS was cured at 70-80° C. for at least 2 hours, then carefully removed from the template disc. Optionally, the PDMS was cured at lower temperatures for longer periods of time—e.g. room temperature for one week—to increase the elasticity and toughness of the cured PDMS mold and improve demolding characteristics. To create flat molds, PDMS solution was poured into a smooth polystyrene dish, as a flat template, and similarly cured and removed. All PDMS molds were ultrasonically cleaned in hydrochloric acid to dissolve any ceramic debris, then ultrasonically cleaned in pure ethanol.

Samples were prepared via hot embossing techniques using biocompatible thermoplastic polymers, such as the following: polycarbonate-based (poly)urethane (PCU; e.g. Carbothane® PC-3595A, Lubrizol Corporation), siliconized polycarbonate urethane (SPCU; e.g. ChronoSil® 85 AL 10% silicone, AdvanSource Biomaterials company), and polypropylene (e.g. Alfa Aesar). In the case of thermoplastic polymeric materials, thin sheets ranging in thickness from 1 to 2 mm, were produced by various standard approaches including solution casting (e.g. first dissolving the polymer in a relevant solvent to create a flowable polymer solution, casting the solution in a flat mold, then evaporating the solvent to achieve a flat sheet), heat molding (e.g. using a heated press to achieve a flat sheet), or extrusion. Discs were punched out of the flat sheets using a circular punch. To emboss the target ceramic microstructures, a polymer disc was sandwiched between flat or microstructured PDMS molds (produced above) in a custom made cylindrical PTFE chamber, and then uniform compressive pressure was applied to the molds on both sides using loaded pistons. Suitable pressure for hot embossing thermoplastic polymers was in the range of 5-50 bar. Embossing constructs were heated at temperatures above their Tg (e.g. 170-220° C.) in an oven for 60 minutes, then allowed to cool naturally to room temperature before carefully demolding. In this way, the desired surface architecture was transferred to both sides of the target material samples. Embossed sample discs were punched out having approximate dimensions of 8 mm diameter and 1 mm thickness.

Samples were also prepared via casting methods using biocompatible thermoset polymers, such as silicone (e.g. Sylgard® 184 PDMS). Depending on the polymer solution to be cast, pre-treatment of the microstructured mold was necessary to allow for demolding of the cast replica. In the present example, surface treatment and passivation of the mold was achieved by first plasma activating the surface of the PDMS mold in a commercially available plasma coater (e.g. Femto PCCE plasma coater, Dienter Electronic company) using the following settings: $O_2$ gas, 0.5 mbar pressure, 100 W power, 60 seconds). After plasma activation, the textured PDMS mold was passivated in 100% ethanol under vacuum until fully evaporated. Other surface treatments could alternatively be applied to assist in demolding, such as silanation. In the present example, PDMS solution (Sylgard® 184, 10:1 w/w base to curing agent) was poured over the treated PDMS mold, then degassed in a vacuum for at least 30 minutes. Continuous pressure was applied, for example using a pressure chamber or weights, and cured at room temperature for 1 week. Alternatively, a strong vacuum could be applied and maintained during room temperature curing. Cured PDMS replicas were easily demolded from the textured PDMS molds using these methods with no adverse cytotoxic demolding agents.

To create reference samples of a commercially available microstructured surface texture, the outer textured PDMS shell of a SilkSurface® breast implant (SS) (Motiva®, Establishment Labs) was used. Implant shell material was glued together using PDMS (Sylgard® 184, 10:1 w/w base to curing agent), with the textured side of the shell facing outward, and cured at 70° C. for at least 2 hours. Discs were punched out with approximate dimensions 8 mm diameter and 1 mm thickness. In this way, textured reference samples similarly possessed surface texture on both sides of the sample disc.

Sample discs were ultrasonically cleaned in pure ethanol for in vitro studies, and additionally sterilized in ethylene oxide gas before in vivo implantation.

Example 1.B—Surface Texture Characterization

The method used to characterize surface texture was 3-D Laser Scanning Confocal Microscopy ("3DLSCM"). 3DLSCM was used to collect 3-D topographic data over a given area on a sample surface. The 3-D data were analyzed following the ISO 25178 standard to quantitatively characterize the surface microtextural features.

The surface texture of produced samples was analyzed using a commercially available Keyence VK-X210 series 3D Laser Scanning Confocal Microscope (consisting of a VK-X250K controller and a VK-X210 Measuring Unit). The controller emitted a measurement laser light source of 408 nm at 0.95 mW. The instrument manufacturers software was used for data collection ("VK Viewer" version 2.8.1.0) and data analysis ("VK Analyzer" and "MultiFile Analyzer" version 1.3.1.120). VK Analyzer and MultiFile Analyzer software was capable of computing extracted characterization parameters in compliance with ISO 25178-2:2012. The 3D surface Laser Scanning Confocal Microscope measured the surface heights of a specimen, and produced a map of surface height (z-directional or z-axis) versus displacement in the x-y plane. The surface map was then analyzed in the software according to ISO 25178-2:2012, from which the various areal surface texture parameters—e.g. Sa, Sq, Sdr, Str, etc—were calculated. These parameters described key characteristics of the embodied surface textures. The instrument was periodically calibrated according to the manufacturers specifications.

To analyze the surface texture, a sample was mounted onto the microscope stage with the surface of the sample oriented orthogonally to the axis of the objective. Measurements were collected using the 150×APO (NA=0.95) objective lens provided with the instrument. This lens was selected based on the manufacturer's recommendation on the required spatial resolution, which in the case of the embodied microstructures was below 1 micron. Data was acquired using the acquisition software's "Expert Mode" wherein the following parameters were set: height scan range was set to encompass the height range of the sample (this can vary from sample to sample depending on the surface topography of each); Z-step size was set to 0.08 μm for the 150× objective; laser intensity and detector gain were optimized for each sample using the autogain feature of the instrument control software (maximized reflected laser signal without causing detector saturation); laser double scan was set to Auto with ND filter set to 100%—only to perform when necessary as judged by the software. This last setting was found useful in reducing optical noise. Measurement mode was set to Surface Profile, Area set to Super-Fine (High-resolution), and images were collected with a resolution of 2048×1536 pixels.

The Z-step size setting in the manufacturer's measurement software corresponds to the optical measurement resolution in the z-direction (i.e., depth/height of the sample surface). As the z-step size decreases, more variation in the height/depth of the sample surface texture can be resolved resulting in higher Sdr and Spd values. However, some of this signal may be generated by optical noise rather than actual depth/height variations in the surface texture. The manufacturer advises to use a minimum Z-step size of 0.08 μm when the 150× objective and super-fine resolution are selected.

The Height Cut Level function is a proprietary feature in the manufacturer's analysis software that eliminates optical noise from the surface measurement. The manufacturer advises that Height Cut Level should always be set to medium when applying the 150× objective. When the Height Cut Level is off or set to low, optical noise can create artificially high Sdr and Spd values. However, when the Height Cut Level is too high (e.g., higher than medium), signal from actual surface features can be eliminated along with more optical noise, thereby lowering Sdr and Spd values.

Using the 150× objective, captured high-resolution images comprised a field of view of approximately 96×72 μm, resulting in an x-y resolution of approximately 0.05 μm/pixel. Measurements using the 150× objective were collected using assembly mode, stitching together 9 individual images (3×3 format), resulting in a total image size of approximately 192×264 μm.

If a larger field of view was required, e.g. 1 mm×1 mm, multiple scans, maintaining the same x-y resolution and z resolution, over the surface were collected and stitched together into a single image for analysis. Consequently, the required scale of areal field of view did not impact the accuracy or precision of the measurements. In other words, the calculated areal surface texture results were similar whether the analysis area was 10 square microns or 1 square millimeters. The measurement file in MultiFile Analyzer software was opened. Manufacturer recommended image processing filters were applied in the Process Image software module to minimize measurement noise and maximize the quality of the surface data: (1) Reference Plane Settings, selecting All Areas; (2) Height Cut Level, medium setting. The surface height image in the surface texture analysis software was opened and S, F, and L filters were applied.

ISO 25178-3:2012 describes a recommended filtration process. The S-filter nesting index (cut-off) value for optical surfaces is user-defined and should be at least three times greater than the lateral (x-y) measurement resolution. In the case of the equipment and objective used, this measurement resolution is 0.05 μm; therefore an S-filter greater than 0.15 μm is appropriate. The nearest value possible in the manufacturer's analysis software is 0.25 μm, so this value was selected for all analyses. As the S-filter nesting index value is increased, calculated areal parameters such as Sdr and Spd generally decrease because a greater amount of the high-frequency signal is filtered out of the measurement.

According to the ISO 25178-3 (2012) standard, the L-filter nesting index (cut-off) value for optical surfaces is also user-defined and should be five times as large as the coarsest surface feature to be quantified in the roughness measurement. Therefore, this value was set to at least 0.1 mm, to eliminate waviness from the roughness measurements.

The following filtering procedure was performed on each image:

For 96×72 μm images acquired using the 150× objective: 1) a Gaussian low pass S-filter with a nesting index (cut-off) of 0.25 μm; 2) an F-operation of plane tilt (auto) correction; and 3) a Gaussian high pass L-filter with a nesting index (cut-off) of 0.1 mm.

For assembled 192×264 μm images, stitched together from 9 individual 96×72 μm images acquired using the 150× objective: 1) a Gaussian low pass S-filter with a nesting index (cut-off) of 0.25 μm; 2) an F-operation of plane tilt (auto) correction; and 3) a Gaussian high pass L-filter with a nesting index (cut-off) of 0.5 mm.

Filters were applied with end effect correction. This filtering procedure produced the S-L surface from which the areal surface texture parameters were calculated. The entire field of view was selected for measurement, and the areal surface roughness parameters were calculated by the Multifile Analyzer software based on the S-L surface. Filtering and parameter calculation was performed according to the according to ISO 25178-2:2012 and explanatory literature (DOI: 10.1007/978-3-642-36458-7_4). The mathematical derivations and descriptions of the surface texture parameters—e.g. Sa, Sz, Sq, Ssk, Sku, Sdr, Spd, Sdq, Sal, and Str—are published in ISO 25178-2:2012.

The surface textures of at least three different locations were scanned and analyzed. The texture values were averaged together and reported to the nearest 0.01 unit.

Example 1.C—Scanning Electron Microscopy

Samples were sputter-coated with a nanolayer of gold, approximately 10 nm thick, and then imaged using a scanning electron microscope (SEM, e.g. Philips XL-30, JEOL IT200). Micrographs were captured at various magnification levels ranging from 500× to 5,000× with typical acceleration voltage of 10-15 keV.

Example 1.D—Water Contact Angle

The water contact angle of produced samples was measured using a commercially available Drop Shape Analyzer instrument (Kruss). A droplet (4 µl) of deionized water was dispensed by the instrument onto the sample surface and allowed to equilibrate for 30 seconds. The contact angle of the droplet was optically calculated via a 2-tangent algorithm in the software according to the manufacturer's instructions. Replicate samples were measured to confirm the results. Measurements were averaged and reported to the nearest 0.1 unit.

Table A shows the surface characteristics of the TCP template materials and the PDMS template materials; the areal surface texture values were measured using 3DLSCM equipped with a 150× objective.

The results as shown in Tables A and B, areal surface texture parameters of ceramic microstructures and polymer replicas were quantified according to the ISO 25178-2:2012 standard using 3DLSCM. In certain essential parameters, the areal surface texture parameters were substantially different than the comparative commercially available material derived from the outer shell of the textured SilkSurface® breast implant (simply, SilkSurface®, SS) and from the materials described in WO2019/118983.

Arithmetic Mean Height (Sa) of the ceramic templates TCP1, TCP2, and TCP3 ranges from 0.77 to 2.65 µm mean values, illustrating that this parameter can be controlled by tuning the process conditions of the ceramic template production. Of particular importance is the capability of achieving low Sa values <1 µm. Following similar trends, Root Mean Square Height (Sq) of TCP1, TCP2, and TCP3 ranges from 0.99 to 3.46 µm mean values. Maximum peak-to-valley height (Sz) of TCP1, TCP2, and TCP3 ranges from 10.98 to 34.51 µm mean values. Comparatively, mean Sa, Sq, and Sz values of SS are 2.11 µm, 2.68 µm, and 21.56 µm, showing in particular that TCP1 presents substantially lower mean values for these parameters versus SilkSurface®.

The template material used to create textured implant materials as disclosed in U.S. Pat. No. 10,595,979 is acellular dermal matrix basal membrane (ADM BM). According to the presented figures in that patent (16A-16D, 17A-17D, 18A-18D), ADM BM possesses surface features ranging from nanometer scale up to microscale. Although no filtering steps are described, it can be inferred from the surface profile plots that if a low-pass S-filter was applied, according to ISO 25178-3 (2012) and referenced standards such as the S-filter applied in the current examples (i.e., Gaussian S-filter with nesting value=0.25 µm), the contribution of the nano-scale features would be eliminated from the calculation of surface parameters. Based on this, one can reasonably expect that ADM BM, and the SilkSurface® material which is a replica thereof, would not possess sufficiently complex surface architecture on the microscale to embody or produce via replication Sdr values greater than 1.0 or Spd values greater than $1\times10^6$ peaks/mm$^2$ while maintaining an Sa value of less than 3.0 µm as described in the current invention.

For the materials described in WO2019/118983 the determined values for Sa are below 3.0 µm and the values for Sdr are below 1.0 when a filter is applied during the performance of the surface roughness test using a Keyence 3D surface Laser Scanning Confocal Microscope according to ISO 25178-2:2012. The results of the tests are given in Table 1 at p. 15 of WO2019/118983.

The first two lines in Table 1 show the surface roughness of samples A and B that were determined using no filter.

However, as soon as a filter is applied during the determination of the surface roughness, as is the case for the samples tested according to embodiment of the present invention, the Sdr values for samples A and B are below 1.0.

Surface skewness (Ssk) of the ceramic templates TCP1, TCP2, and TCP3 ranges from −0.35 to −0.66 indicating a negative skew of surface features. This means that the surfaces comprise relatively more valleys (i.e. pores) than peaks. When Ssk is >0, this means the surface comprises relatively more peaks than valleys. Surface kurtosis (Sku) of the templates TCP1, TCP2, and TCP3 ranges from 3.40 to 4.68 indicating a surface of relatively sharp sloping peaks rather than gradual bumps. This is meaningful in reducing tribological friction of a surface. The literature teaches that when Sku increases and Ssk becomes more negative, the coefficient of friction is minimized. Comparatively, Ssk and Sku of SilkSurface® are 0.16 and 3.28, suggesting relatively higher coefficient of friction versus the ceramic templates according to the literature (DOI: 10.1080/10402004.2016.1159358).

The surface developed interfacial ratio (Sdr) of the ceramic templates TCP1, TCP2, and TCP3 ranges from 1.57 to 21.10 mean values, indicating an increase of surface area ranging from 157% to 2,110% for the TCP templates versus a perfectly flat surface. Sdr is the quantification of the percentage of additional surface area contributed by the texture as compared to an ideal plane the size of the measurement region, and in this way relates to the complexity of the surface. An Sdr value of 1.00 means a measured surface exhibits 100% more surface area than a perfectly flat material of the same measurement area. The surface peak density (Spd) of the ceramic templates TCP1, TCP2, and TCP3 ranges from, on average, $2.09\times10^6$ to $3.03\times10^6$ peaks/mm$^2$, showing the extremely high density of surface peaks of the templates. Depending on the application, a low Spd may result in higher localized contact stresses resulting in possible pitting and debris generation. In applications involving sliding components, a high density of surface peaks are needed to reduce friction while maintaining a reasonable load distribution. The surface root mean square gradient (Sdq) of the ceramic templates TCP1, TCP2, and TCP3 ranges from, on average, 2.03 to 8.07. Sdq is a general measurement of the slopes which comprise the surface and may be used to differentiate surfaces with similar average roughness. The Sdq of a perfectly flat surface is 0. Sdq is affected both by texture amplitude and spacing. Thus for a given Sa, a wider spaced texture will result in a lower Sdq value than a surface with the same Sa but finer spaced features. Taken together, Sdr, Spd, and Sdq collectively represent the complexity of the surface. In comparison, the mean Sdr, Spd, and Sdq values of SilkSurface® are 0.77, $0.73\times10^6$ peaks/mm$^2$, and 1.45—all substantially lower than any of the ceramic templates. Collectively, these values show that the SilkSurface® surface is substantially less complex than the ceramic templates.

For the materials described in WO2019/118983, the determined values for Sdr are below 1.0 and the determined values for Spd are below $1.00\times10^6$ peaks/mm$^2$ when a filter is applied during the performance of the surface roughness test using a Keyence 3D surface Laser Scanning Confocal Microscope according to ISO 25178-2:2012. The results of the tests are given in Table 1 at p. 15 of WO2019/118983.

The first two lines in Table 1 show the surface roughness of samples A and B that were determined using no filter. However, as soon as a filter is applied during the determination of the surface roughness, as is the case for the samples tested according to an embodiment of the present invention, the Sdr and Spd values for samples A and B are below 1.0 and $1.00 \times 10^6$ peaks/mm$^2$, respectively.

Surface autocorrelation length (Sal) of the ceramic templates TCP1, TCP2, and TCP3 ranges from, on average, 7.48-11.57 µm. Sal is a quantitative measurement of the minimum distance along the surface between two locations whose textures that are statistically different from each other, i.e. minimal correlation. The surface texture aspect ratio (Str) of the ceramic templates TCP1, TCP2, and TCP3 ranged from, on average, 0.66 to 0.85, indicative of isotropic surface textures. Str is a measure of the spatial isotropy or directionality (also, lay) of the surface texture. For a surface with perfect directionality, Str=0.00; for a surface that is perfectly isotropic, Str=1.00. In comparison, the mean Sal and Str values of SilkSurface® are 21.73 and 0.78.

Representative SEM micrographs of ceramic templates, as shown in FIG. 1, demonstrate that these surfaces comprise an isotropic distribution of interconnected, spheroidal grains and pores arising from the specific conditions of the production process. In general, TCP1 possesses the smallest features—both grains and pores—versus TCP2 and TCP3, which are substantially smaller than 1 µm on average. Despite the randomly occurring network of fused grains and pores visible at high magnification, the surface textures all visually appear to be uniformly distributed and structured at lower magnifications, evident of high production purity and consistency. The high complexity, peak density, and specific surface area can also be appreciated for all ceramic templates, particularly in high magnification micrographs. In comparison to other known microstructures in the art, there is no machined direction array pattern or discernible demarcation between the granular protrusions and interdigitated porous valleys. The topographical features are both randomly and homogeneously distributed over the surface at both high and low magnifications.

Figure 2:
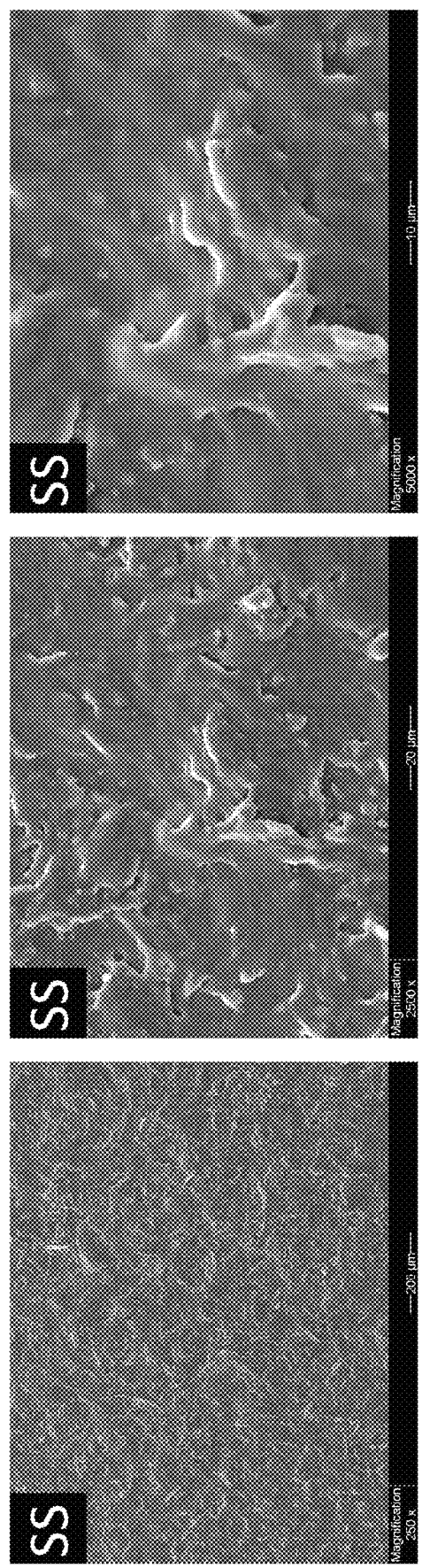
FIG. 2 shows scanning electron micrographs of the Silk-Surface® implant textured surface according to one embodiment of the present invention.

In contrast, representative SEM micrographs of SilkSurface®, as shown in FIG. 2, demonstrate this surface comprises a random array of protruding hills and irregular depressions of varying nodular and crescent form and size. It is evident that the complexity of the surface is relatively low compared to the ceramic template surfaces, particularly from the apparent areal density of protrusive and receding elements, as well as the perceivable interfacial area. The irregularity of the surface feature morphology is also comparatively high versus the ceramic templates, as is visually apparent in the high magnification images. At low magnifications, the SilkSurface® surface appears heterogenous and isotropic.

Figure 3:
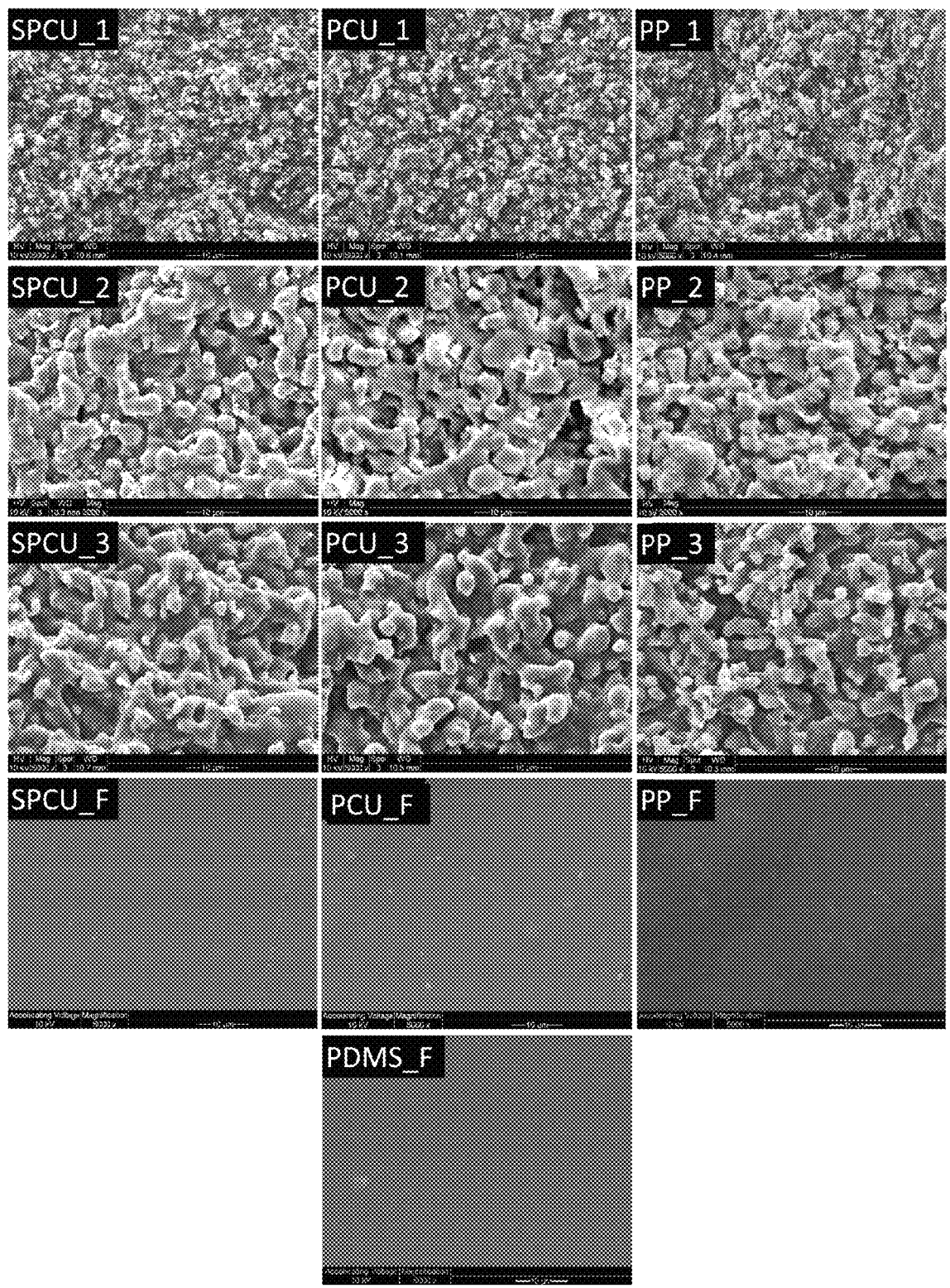
FIG. 3 shows scanning electron micrographs of microstructured and flat SPCU, PCU and PP polymer surfaces according to one embodiment of the present invention.
Figure 4:
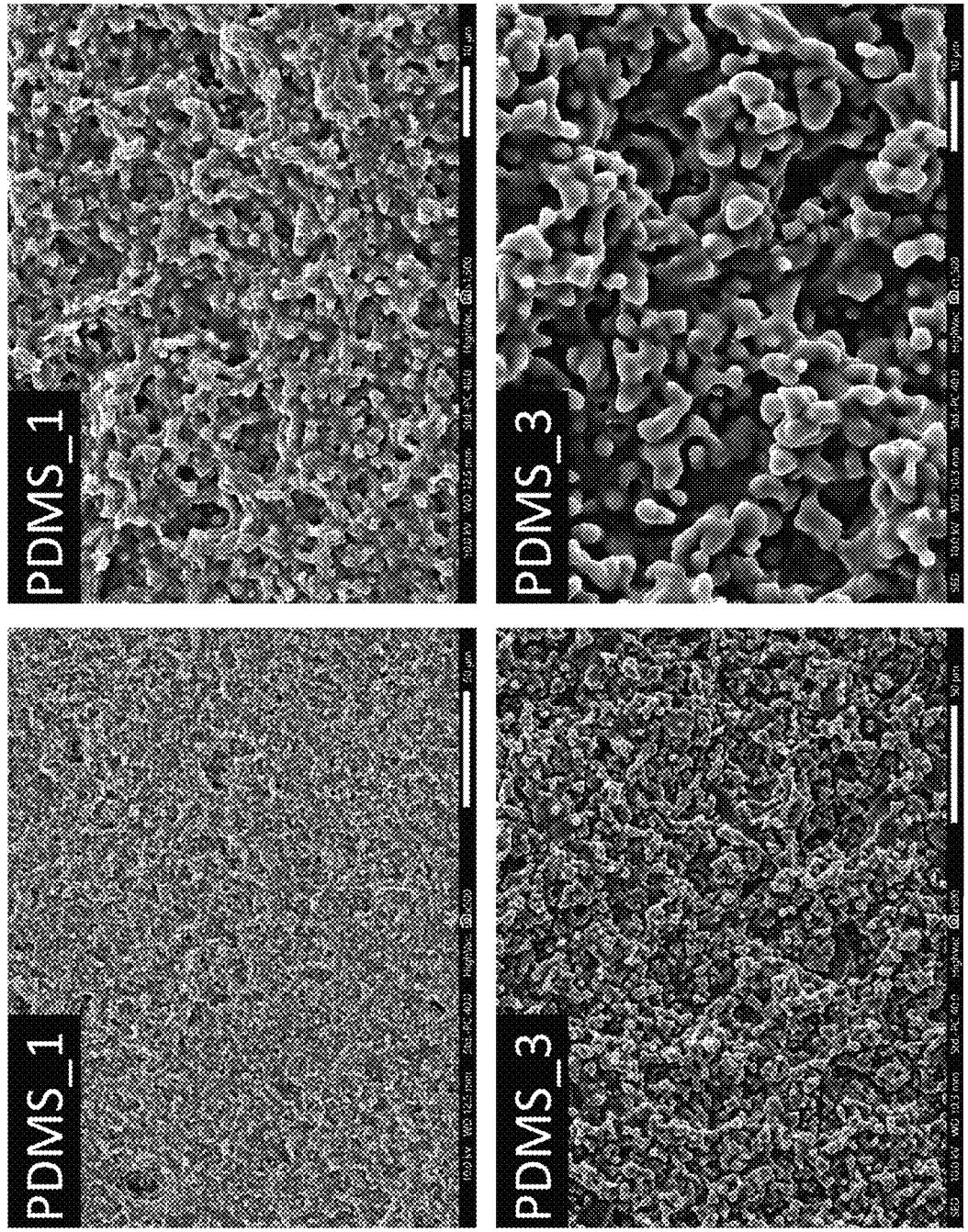
FIG. 4 shows scanning electron micrographs of microstructured PDMS surfaces according to one embodiment of the present invention.
Figure 5:
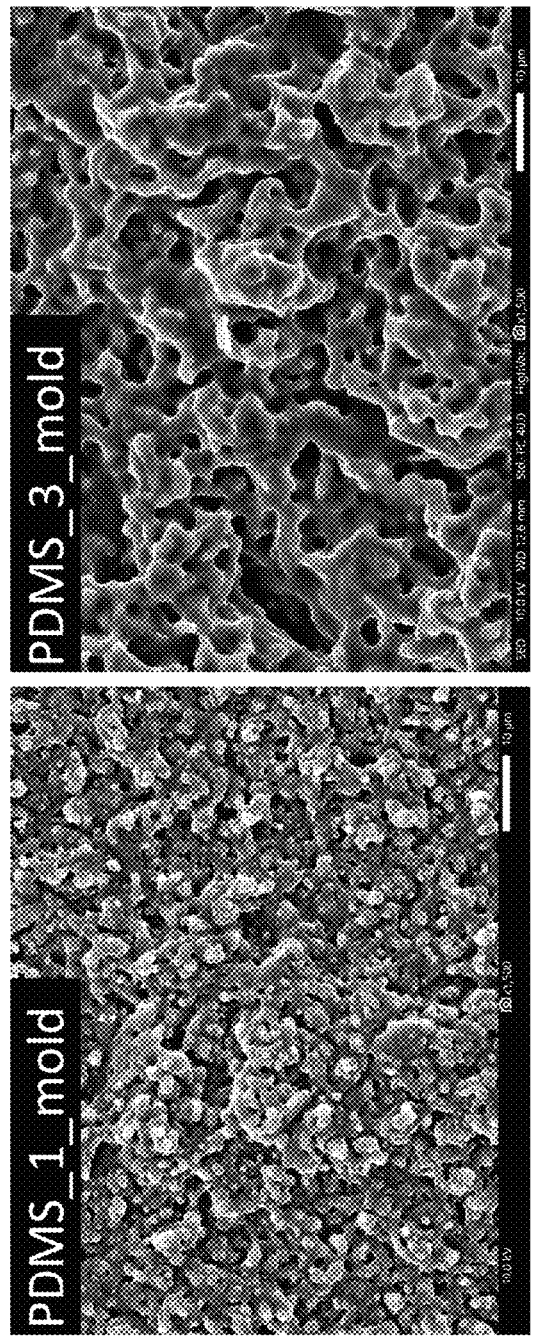
FIG. 5 shows scanning electron micrographs of microstructured PDMS molds according to one embodiment of the present invention.
Figure 16:
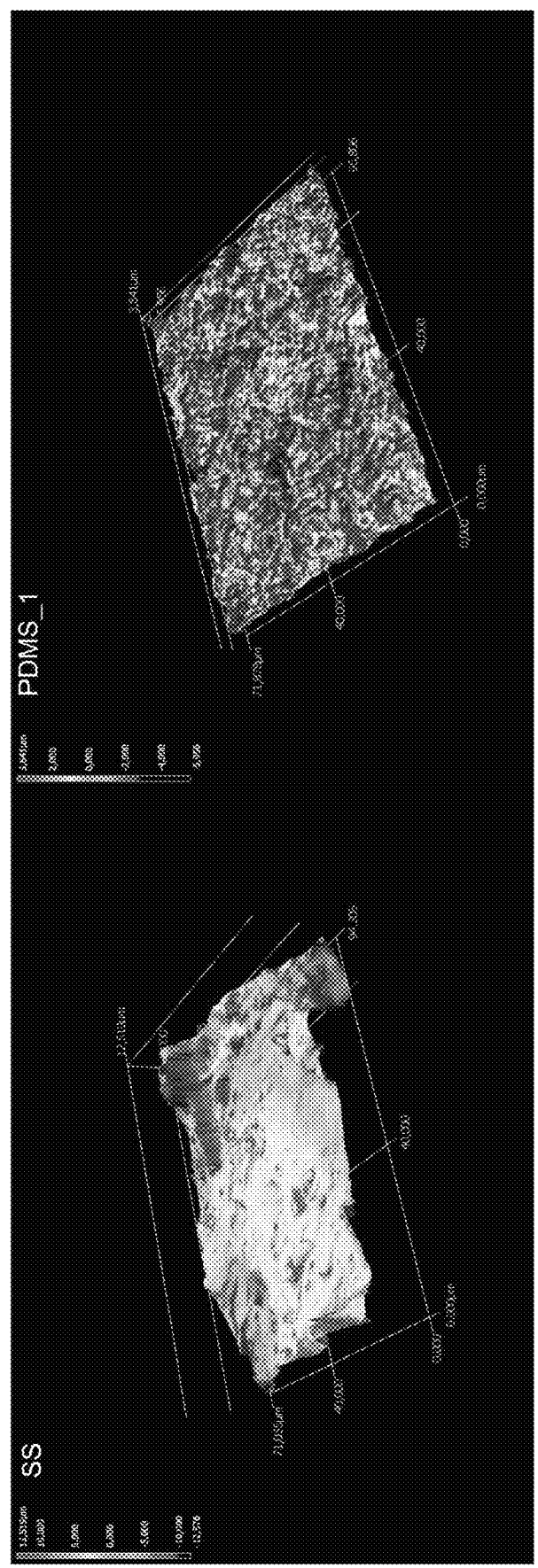
FIG. 16 illustrates 3D surface scans produced by 3DLSCM analysis showing that microstructured features are present on SilkSurface® breast implant shell (left panel) and a textured polymeric material (PDMS_1) according to one embodiment of the present invention (right panel).

The microstructured ceramic and flat template surface structures are replicated in various medical polymers including SPCU, PCU, PP, and PDMS using both hot-embossing and casting methods. As shown in the SEM micrographs (FIG. 3, 4), replication of ceramic template surface microstructure—in terms of feature size, shape, and arrangement—occurs consistently across the various polymers with good fidelity. The template ceramic surface microstructures are particularly well replicated in PDMS (FIG. 4). Replication of microstructured templates is enabled by high-fidelity PDMS molds produced by soft lithography; similar grain and pore feature sizes are observed with the inverse form of the originating templates (FIG. 5). In concert with these results, areal surface texture parameters as measured by 3DLSCM (Table B) confirm that generally the key surface texture parameter values—Sa, Sz, Sq, Ssk, Sku, Sdr, Spd, Sdq, Sal, and Str—are well preserved and within reasonable range of those of the ceramic templates. 3D surface scans produced by 3DLSCM analysis show that SilkSurface™ and microstructured PDMS according to embodiments of the invention possess visibly and quantifiably different surface textures (FIG. 16). The microstructured PDMS surface possesses considerably higher peak density, finer feature size, and more consistent and homogenous distribution of peaks and valleys as compared to SilkSurface®, which shows an irregular distribution of comparatively larger bumps and grooves.

Water contact angle measurement of microstructured and flat polymers (Table B) showed that increasing microstructural roughness results in increasing hydrophobicity for all the polymer types tested. This result is important because highly hydrophobic surfaces have been shown to resist microbial adhesion and biofilm formation.

TABLE A

|   | Material | Sa µm | Sz µm | Sq µm | Ssk | Sku | Sdq | Sdr | Spd 1/mm$^2$ | Spc 1/mm | Str | Sal µm |
|---|---|---|---|---|---|---|---|---|---|---|---|---|
| CE A | SilkSurface ®, SS | 2.11 | 21.56 | 2.68 | 0.16 | 3.28 | 1.45 | 0.77 | 0.73E+06 | 12385.67 | 0.78 | 21.73 |
| 1a | TCP1 | 0.77 | 10.98 | 0.99 | −0.66 | 4.68 | 2.03 | 1.57 | 2.91E+06 | 17545.75 | 0.84 | 7.48 |
| 2a | TCP2 | 1.57 | 16.98 | 2.00 | −0.35 | 3.40 | 3.17 | 3.43 | 2.09E+06 | 26058.67 | 0.85 | 8.44 |
| 3a | TCP3 | 2.65 | 34.51 | 3.46 | −0.54 | 4.59 | 8.07 | 21.10 | 3.03E+06 | 99736.09 | 0.66 | 11.57 |

TABLE B

|   | Material | Sa µm | Sz µm | Sq µm | Ssk | Sku | Sdq | Sdr | Spd 1/mm$^2$ | Spc 1/mm | Str | Sal µm | Water contact angle degress, ° |
|---|---|---|---|---|---|---|---|---|---|---|---|---|---|
| CE A | SilkSurface ®, SS | 2.11 | 21.56 | 2.68 | 0.16 | 3.28 | 1.45 | 0.77 | 0.73E+06 | 12385.67 | 0.78 | 21.73 | 126.2 |
| CE B | PDMS_F | 0.01 | 0.40 | 0.01 | 3.22 | 63.38 | 0.04 | 0.00 | 5.59E+06 | 500.46 | 0.22 | 2.05 | 123.5 |
| CE C | SPCU_F | 0.02 | 1.06 | 0.03 | 2.51 | 43.35 | 0.04 | 0.00 | 2.90E+06 | 280.12 | 0.26 | 35.63 | 111.7 |
| CE D | PCU_F | 0.02 | 0.95 | 0.03 | 1.23 | 17.92 | 0.04 | 0.00 | 2.62E+06 | 266.85 | 0.28 | 37.24 | 104.1 |
| CE E | PP_F | 0.64 | 8.19 | 0.81 | −0.32 | 3.69 | 0.12 | 0.01 | 2.21E+05 | 518.59 | 0.77 | 26.13 | 110.0 |

TABLE B-continued

| | Material | Sa μm | Sz μm | Sq μm | Ssk | Sku | Sdq | Sdr | Spd 1/mm$^2$ | Spc 1/mm | Str | Sal μm | Water contact angle degress, ° |
|---|---|---|---|---|---|---|---|---|---|---|---|---|---|
| 1b | SPCU_1 | 0.80 | 9.06 | 1.04 | −0.89 | 4.47 | 1.77 | 1.19 | 2.44E+06 | 13016.68 | 0.92 | 7.19 | 127.8 |
| 1c | PCU_1 | 0.86 | 11.40 | 1.08 | −0.61 | 4.07 | 1.72 | 1.12 | 2.22E+06 | 12353.98 | 0.91 | 9.66 | 116.6 |
| 1d | PP_1 | 1.09 | 10.19 | 1.36 | −0.52 | 3.07 | 2.03 | 1.53 | 2.84E+06 | 17958.12 | 0.43 | 12.58 | 123.4 |
| 1e | PDMS_1 | 1.22 | 12.36 | 1.53 | −0.61 | 3.45 | 1.66 | 1.04 | 1.74E+06 | 13123.45 | 0.65 | 8.97 | n.d. |
| 2b | SPCU_2 | 1.75 | 17.42 | 2.21 | −0.30 | 3.15 | 3.06 | 3.24 | 2.34E+05 | 25328.43 | 0.90 | 12.03 | 129.2 |
| 2c | PCU_2 | 1.55 | 21.21 | 2.00 | −0.74 | 4.05 | 3.13 | 3.30 | 1.66E+06 | 30462.04 | 0.75 | 10.83 | 118.1 |
| 2d | PP_2 | 1.53 | 16.25 | 1.92 | −0.21 | 3.04 | 2.91 | 2.95 | 2.27E+06 | 23650.70 | 0.89 | 8.03 | 133.4 |
| 3b | SPCU_3 | 2.43 | 23.46 | 3.01 | −0.26 | 2.83 | 3.64 | 4.32 | 1.69E+06 | 29521.25 | 0.81 | 12.20 | 130.6 |
| 3c | PCU_3 | 2.63 | 25.01 | 3.31 | 0.00 | 3.05 | 4.20 | 5.62 | 1.67E+06 | 29460.49 | 0.94 | 14.32 | 121.0 |
| 3d | PP_3 | 2.46 | 27.88 | 3.09 | 0.00 | 3.05 | 5.48 | 9.54 | 2.39E+06 | 44100.88 | 0.93 | 11.68 | 138.2 |
| 3e | PDMS_3 | 2.42 | 27.23 | 3.06 | 3.37 | 3.45 | 5.79 | 10.89 | 1.88E+06 | 56375.68 | 0.81 | 12.13 | n.d. |

2: In Vivo Performance

Example 2.A—In Vivo Implantation and Histological Processing

Discs were implanted in the dorsal subcutaneous fat layer of Bama minipigs. With the permission of the local ethic committee [SYXK (III) 2019-189-AS2019-045], surgical implantation was performed under general anesthesia (with intravenous injection of pentobarbital sodium, 30 mg/kg body weight) and sterile conditions on Bama miniature pigs (n=5; 6 months old, 20±5 kg weight, both male and female). In brief, following anesthesia, longitudinal skin incisions were made on the back beside the spine, and subcutaneous tissue pouches, spaced>2 cm apart, were subsequently made in the fat layer using a scalpel on both sides of the skin incision. Sterile disc implants (diameter=8 mm, thickness=1 mm) were inserted into the subcutaneous pockets—one implant per pocket—using forceps. Pockets were sutured tightly closed using resorbable PGA suture (4-0), and the skin incision was finally sutured with silk suture (4-0). The skin wounds were sterilized with iodine and penicillin was intramuscularly injected for 3 consecutive days to prevent infection. A second surgical implantation identical to the first was performed 13 weeks after the first surgical operation. Four weeks after the second surgical operation, the animals were sacrificed with an overdose of sodium pentobarbital and implants were harvested with surrounding tissues. The harvested samples with implanted durations of 4 weeks and 17 weeks were fixed in 10% buffered formalin, dehydrated in a graded ethanol series, embedded in poly(methyl methacrylate) (PMMA, Cool-Set, Aorigin, Chengdu, China). Sections (~20 μm thick), oriented cross-sectionally through the discs, were made with histological diamond saw (SAT-001, Aorigin, Chengdu, China) and stained with methylene blue/basic fuchsin or hematoxylin/eosin. The stained sections were then digitized with scanning microscopy (Austar43, AiMco, Xiamen, China) at 10× magnification for histological evaluation and histomorphometry. To view the collagen, sections were scanned to polarized overview images using a slide scanner (Konica Minolta Elite 5400 II, Japan) and polarized film.

Example 2.B—Capsule Thickness and Composition

The thickness of the fibrous capsules and comprising capsule tissue layers at 4 and 17 weeks was measured using AxioVision software (Carl Zeis, version 4.9.1) at a magnification level of 5×. Thickness measurements were made at 15 different locations surrounding each implant from a representative section, arising from three histological sections per implant. Generally, two distinct tissue layers were evident within the capsule: the inflammatory layer, mainly made up of mononuclear leukocytes (e.g. macrophages), and the denser fibrous layer, mainly made up of fibrous tissue oriented in a parallel direction to the surface of the implant. Total capsule thickness measurements were made perpendicular from the material surface outward to the point where the capsule ceased and native tissue such as fat or dermal tissue began. Inflammatory layer thickness measurements were similarly made but only to the transition point between the loose inflammatory layer and the denser fibrous layer of the capsule. The dense fibrous layer was calculated as the difference between the total capsule thickness and the inflammatory layer thickness (e.g. total capsule thickness minus inflammatory layer thickness).

Example 2.0—Capsule Density Measurement

The tissue density of the fibrous capsules formed at 4 and 17 weeks was characterized by measuring the chromatic saturation levels in the histological sections corresponding to stained collagenous tissue. ImageJ software was used for all image processing and analysis. Similar methods have been previously described in the literature (Chen Y, et al. Int J Clin Exp Med 2017; 10(10):14904-14910). The chromatic saturation of a particular histologically stained tissue section (e.g. using a chromogenic dye) can be linked to the areal density of that tissue given that more densely packed tissue will bind more chromogen than less densely packed tissue of the same area and thickness.

Representative images of the fibrous capsule were captured at 22× digital magnification at three different locations around the implant surface. Representative images of the dermal tissue were similarly captured at 22× magnification at three locations in the same histological section as a reference for the standard chromatic saturation of collagenous tissue. Image acquisition was conducted using standard digital slide scanner software (e.g. HD Scanner software) and exported in 24-bit RGB TIFF format. Acquired images were imported into ImageJ and color deconvoluted into RGB channels using the Color Deconvolution plugin (version 2). In this way, the red color channel corresponding to fuchsin-stained collagenous tissue could be independently analyzed. The deconvoluted red-channel of each image was first converted into HSB (hue-saturation-brightness) format so the saturation values of each image could then be measured using the Measure function in ImageJ. The Measure function provides a measured output of mean (average) pixel intensity on a scale from 0 to 255, corresponding to standard 8-bit 256 shade grayscale; in this context, a pixel intensity of 255 represents complete saturation and 0 represents complete unsaturation. Mean saturation levels of replicate locations within the same capsule were averaged and normalized against the average of mean saturation levels measured in the dermal tissue of the same histological section. In this way, differences in section thickness as well as differences in animal tissue structure were normalized in the measurements. Averaged normalized chromatic saturation values of microstructured samples in each material group were then divided by the mean color saturation values of respective flat samples within that same material group, resulting in relativized, normalized chromatic saturation values (e.g. the normalized chromatic saturation values of SPCU_1 and SPCU_3 each divided by the normalized chromatic saturation value of SPCU_F; the normalized chromatic saturation values of PCU_1 and PCU_3 each divided by the normalized chromatic saturation value of PCU_F; the normalized chromatic saturation values of PP_1 and PP_3 each divided by the normalized chromatic saturation value of PP_F; the normalized chromatic saturation values of SS divided by the normalized chromatic saturation value of PDMS_F). Resulting relativized, normalized chromatic saturation values are thus reported as a relative percentage vs. respective flat values.

Example 2.D—Results of the In Vivo Performance

Microstructured and flat polymeric sample discs were implanted in the dorsal subcutaneous tissue of Bama minipigs to study their tissue response, according to the study design outlined in Table C. The study was designed to evaluate the biological response to ceramic surface microstructure replicated in different polymers, made up of different material chemistries. For each polymer cluster (e.g. SPCU groups, PCU groups, PP groups), sample groups comprised either TCP1, TCP3, or a flat surface structure. Flat PDMS (PDMS_F) and textured SilkSurface® (SS), which is composed of PDMS (DOI: 10.1093/asj/sjx150), were also included as relevant benchmarks in the art. In this way, the effects of surface structure and surface chemistry were decoupled so that the effects of surface structure could be more universally appraised. Relative comparisons could be made within polymer groups to discern the specific impact of surface structure on tissue response, specifically: SPCU_1 and SPCU_3 versus SPCU_F; PCU_1 and PCU_3 versus PCU_F; PP_1 and PP_3 versus PP_F; SS versus PDMS_F.

Figure 6:
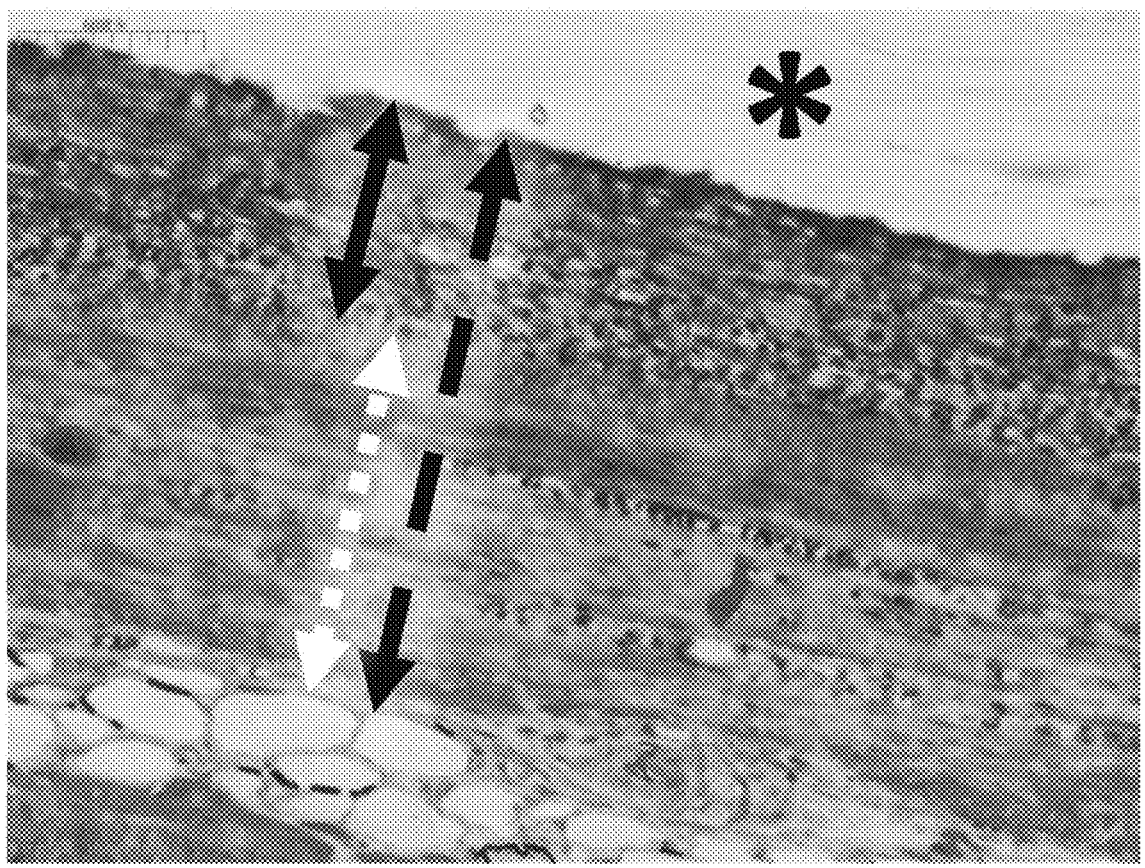
FIG. 6 is a representative histological micrograph depicting a typical fibrous capsule formed around polymer implants. The star denotes the implant, the solid arrow denotes the inflammatory layer (stained blue in the original color image), the short dashed arrow denotes the fibrous layer (stained fuchsin in the original color image), and the long dashed arrow denotes the total capsule thickness. The micrograph was captured at 10× magnification according to one embodiment of the present invention.

The subcutis, located below the dermis, is principally made up of vascularized adipose tissue and is a relevant location to study the foreign body response to biomaterials. Moreover, the Bama minipig is a well-accepted species model for understanding the human immune system. Implanted samples were recovered after 4 and 17 weeks implantation and processed for histology as described in the methods. The fibrous capsule formed around the implants was measured in stained histological tissue sections using specialized software. The fibrous capsule formed around the implants due to the foreign body response is generally found to comprise two distinct tissue layers, as depicted in FIG. 6: (1) the inflammatory layer, principally composed of mononuclear leukocytes and occasional multinucleated giant cells immediately apposed to the implant surface, and (2) the fibrous layer, principally composed of fibroblastic cells oriented in a parallel manner to the surface of the implant. Typically, the inflammatory layer is well vascularized and more densely populated by cells, while the fibrous layer is less vascularized, and less densely populated by cells. The fibrous capsule was quantified in terms of total thickness, as well as constituent inflammatory and fibrous layers as shown in FIG. 6 to characterize the capsule tissue morphology as well as composition.

At 4 and 17 weeks, the thickness of capsules formed around microstructured and flat polymeric samples were approximately similar within the same polymer compositional groups (e.g. SCPU_1 vs. SPCU_3 vs. SPCU_F) (Table C). Comparison between SS and PDMS_F were also made because SS is also composed of PDMS. In agreement with the other polymer groups, there was no apparent difference in average capsule thickness between SS and PDMS_F groups.

Figure 7:
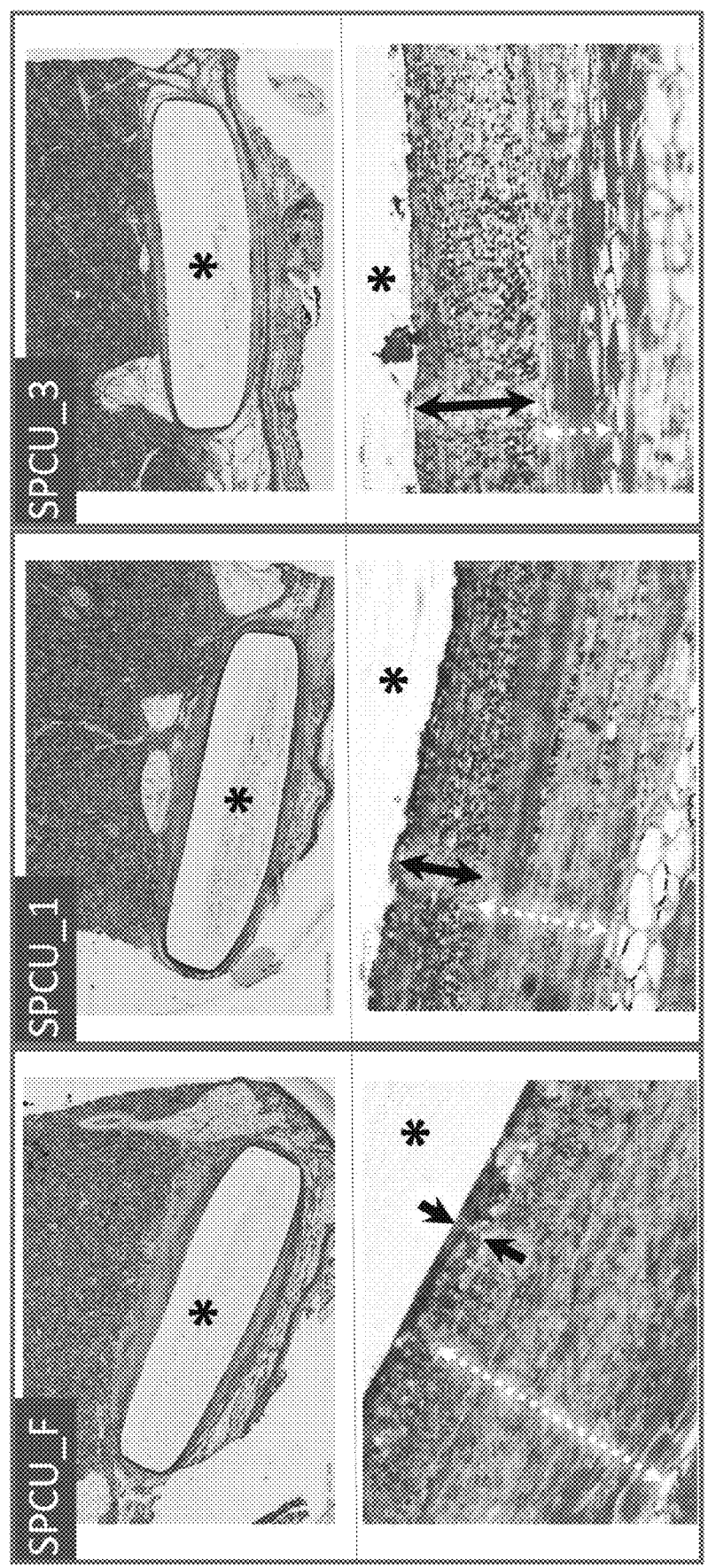
FIG. 7 are representative histological micrographs depicting typical fibrous capsules formed around microstructured and flat polymer implants at 4 weeks. Stars denote the implants, solid arrows denote inflammatory layers (stained blue in the original color images), and dashed arrows denote fibrous layers (stained fuchsin in the original color images). Micrographs were captured at 0.4× (top row) and 10× (bottom row) magnifications according to one embodiment of the present invention.
Figure 8:
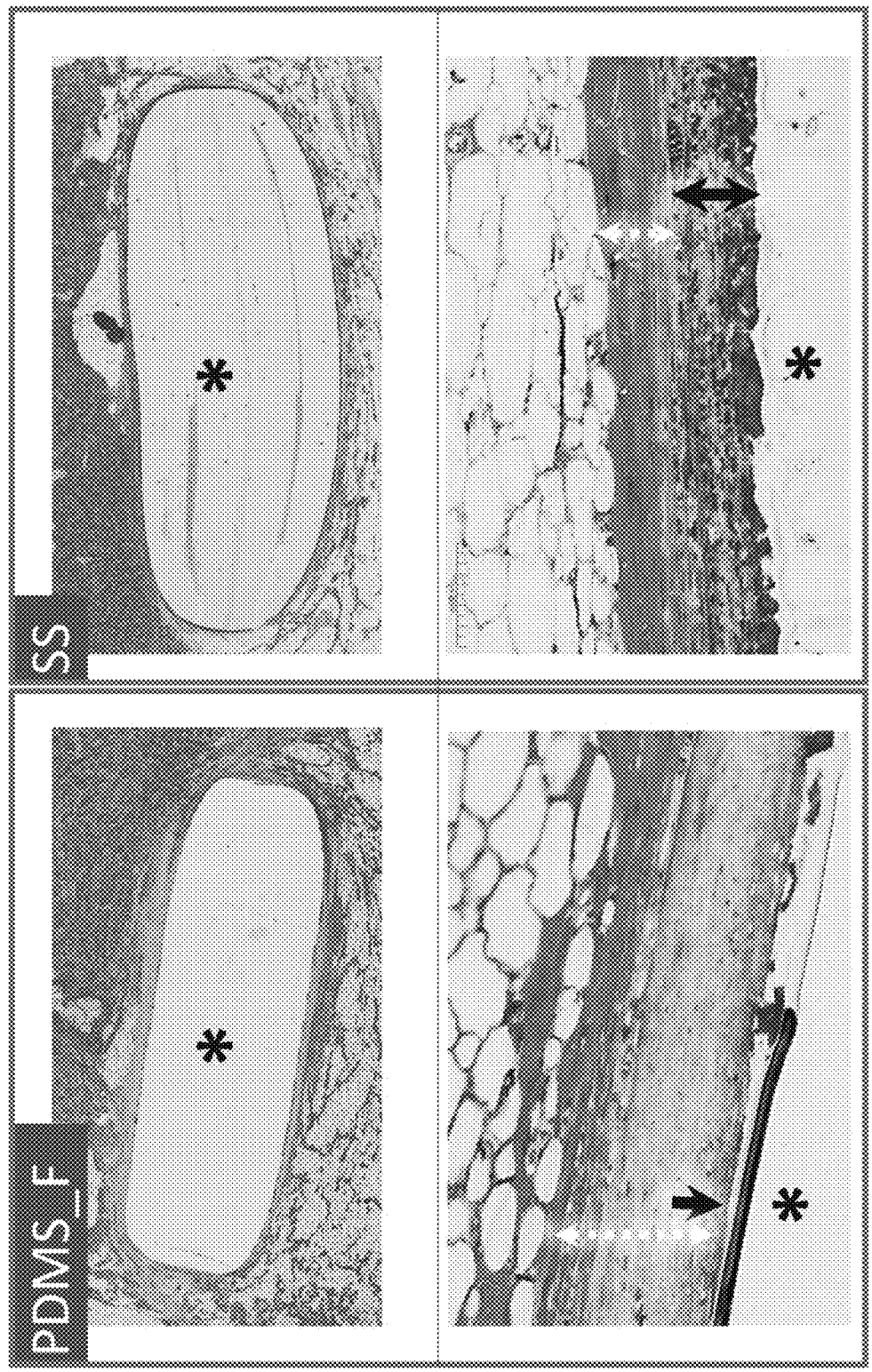
FIG. 8 are representative histological micrographs depicting typical fibrous capsules formed around flat PDMS (PDMS_F) and SilkSurface® (SS) implants at 4 weeks. Stars denote the implants, solid arrows denote inflammatory layers (stained blue in the original color images), and dashed arrows denote fibrous layers (stained fuchsin in the original color images). Micrographs were captured at 0.4× (top row) and 10× (bottom row) magnifications according to one embodiment of the present invention.

There were, however, differences in capsule composition, as defined by inflammatory and fibrous layer thicknesses, in response to the surface structure. At 4 weeks, sample groups incorporating microstructured surfaces exhibited substantially higher mean inflammatory layer thickness versus the respective flat reference groups (e.g. from Table C: the mean inflammatory layer thickness of PCU_1 and PCU_3 was roughly 100% greater than PCU_F). This systematic effect of surface structure, demonstrated across all evaluated polymer chemistries, points to a powerful, universal role of surface microstructure directing the immune response. A similar relationship in inflammatory layer thickness was observed for SilkSurface, which was ~83% greater than flat PDMS (Table C). FIGS. 7 and 8 present representative micrographs of histological sections stained with basic fuchsin/methylene blue, which depict these global differences in inflammatory layer thickness at 4 weeks.

In concert with increased inflammatory layer thickness, mean fibrous layer thickness decreased by up to ~45% in response to surface microstructure at 4 weeks for all polymer clusters (e.g. SPCU, PCU, and PP). For example, mean fibrous layer thickness for SPCU_1 and SPCU_3 ranged from 152-161 microns versus 252 microns for SPCU_F (Table C). In comparison, mean fibrous layer thickness of SS implants decreased by ~15% versus flat PDMS_F. FIGS. 7 and 8 present representative micrographs of histological sections stained with basic fuchsin/methylene blue, which depict these global differences in fibrous layer thickness at 4 weeks.

By 17 weeks, the inflammatory layer thickness systematically decreased for all microstructured groups by similar proportions relative to their 4 week values, illustrating healthy restitution of temporal inflammation to a lower, equilibrium state. Fibrous layer thickness also equilibrated to similar levels within polymer groups, irrespective of surface structure as shown in Table C.

In the literature, it is known that capsule thickness alone may not be a determining factor of maladies such as capsular contracture. Compositional characteristics of the capsule such as capsular collagen density and alignment may also play important roles. To probe the capsule composition deeper, two different methods were employed: chromatic saturation measurement and polarized light microscopy. Chromatic saturation measurement was conducted using image analysis software and corresponds to the amount of histologic stain taken up by the tissue section during staining. Qualitatively, it is apparent that densely organized dermal tissue, which is principally composed of collagen, stains deep fuchsia following staining with basic fuchsin and methylene blue dyes. By normalizing the chromatic saturation level of the capsule fibrous layer to that of neighboring dermal tissue, the relative collagen content of the capsule can be quantitatively measured from density of chromatic saturation. Moreover, polarized light microscopy is often used in the art to analyze collagen density and alignment, based on the birefringence properties of collagen's morphology. Under polarized light, collagen reflects the polarized light and can therefore be visualized.

Figure 9:
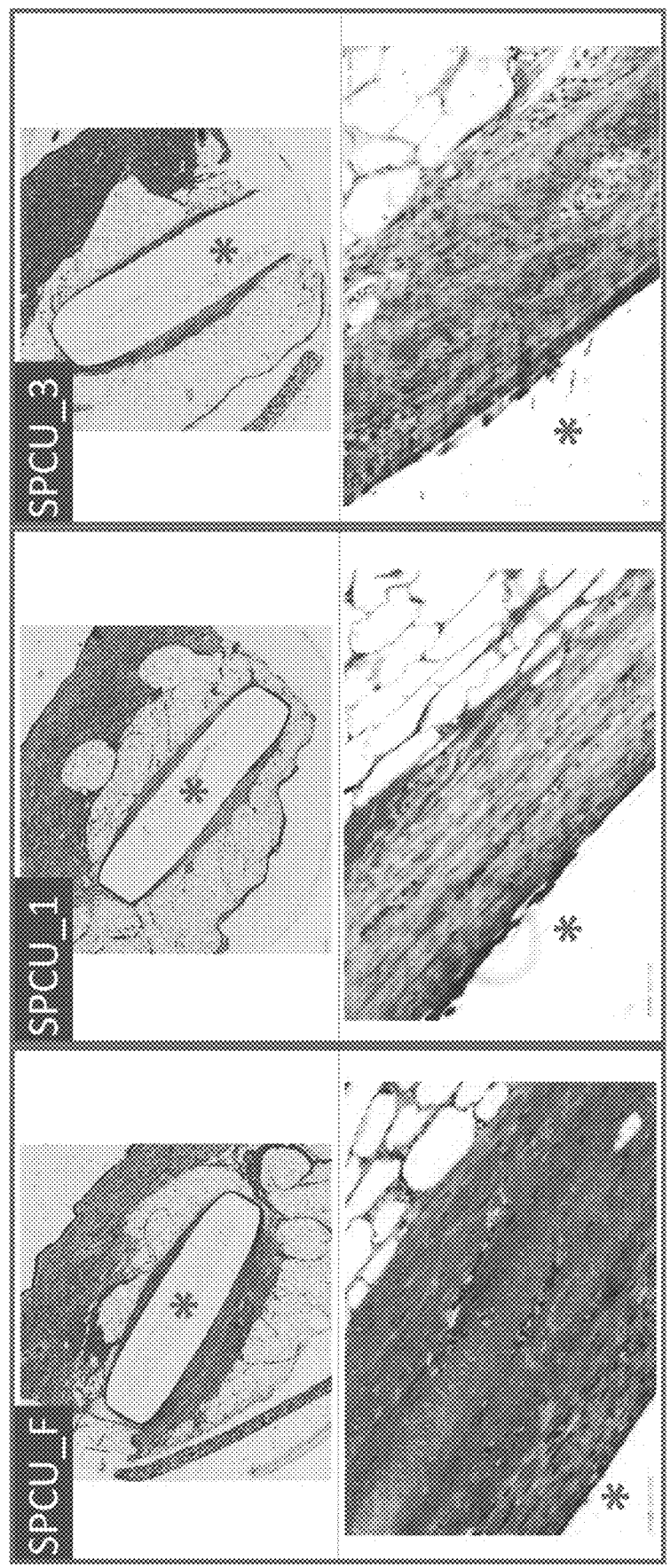
FIG. 9 are representative histological micrographs depicting typical fibrous capsules formed around microstructured and flat polymer implants at 17 weeks. Stars denote the implants. Micrographs were captured at 0.4× (top row) and 10× (bottom row) magnifications according to one embodiment of the present invention.
Figure 10:
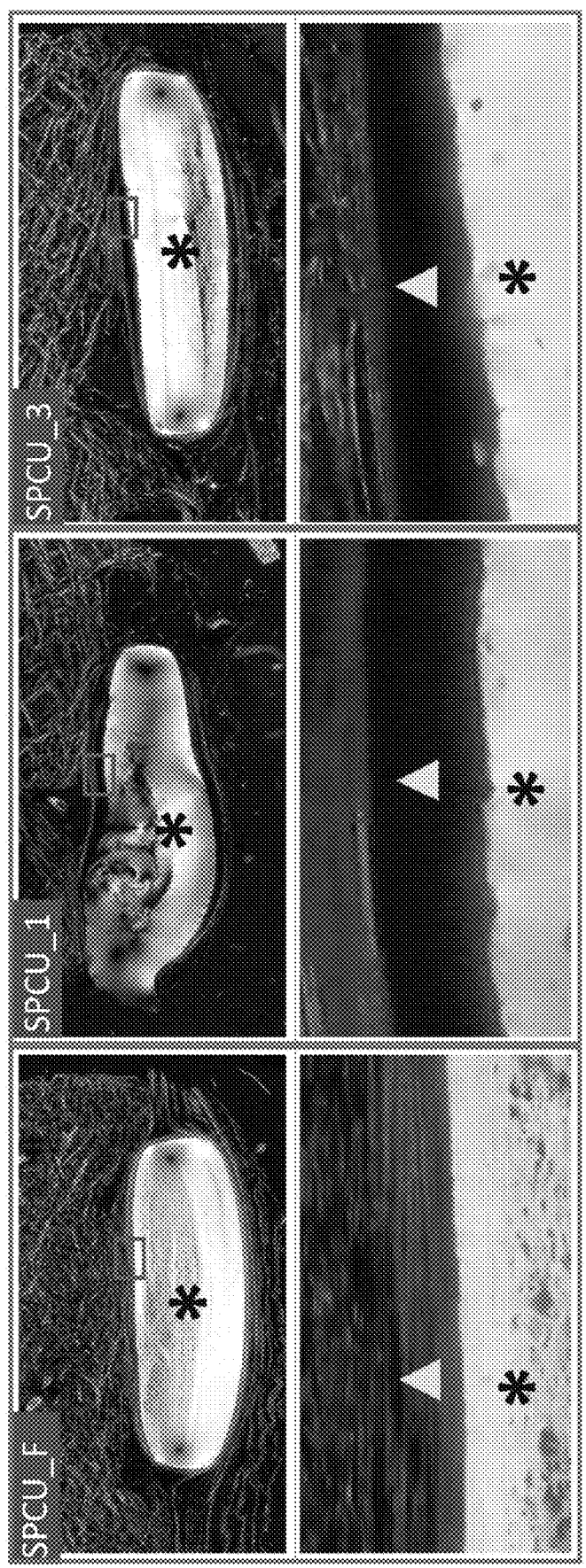
FIG. 10 are representative histological polarized micrographs depicting typical fibrous capsules formed around microstructured and flat polymer implants at 4 weeks. Stars denote the implants, and triangles denote the capsule immediately apposed to the implant surface. Micrographs were captured at 0.4× (top row) and 20× (bottom row) magnifications according to one embodiment of the present invention.

Using both methods, it was observed that the microstructured polymeric surfaces reduce the density of fibrous capsules versus flat surfaces at both 4 and 17 weeks. Quantitatively, chromatic saturation analysis showed that capsule fibrous density was significantly reduced in microstructured groups versus their respective flat reference groups—in some cases by more than 50% (e.g. at 4 weeks, PCU_1=46% and PCU_3=45%; both relativized versus the normalized chromatic saturation level of PCU_F at 4 weeks) (Table C). This difference in fibrous capsule density is evident in the histological micrographs presented in FIG. 9, in that the chromatic saturation (i.e. richness of color) of the histological stain is clearly greater for the flat implant versus that of the microstructured implants. Qualitatively, these results were confirmed using polarized light microscopy, which showed that the capsular tissue layer closest to the microstructured surfaces is appreciably devoid of collagen (FIG.

capsule density, fibrous capsule thickness, or fibroblast viability on the medical device implant textured surface as compared to a medical device implant such as a breast implant under the same conditions and of the same dimensions that have no textured surface or a textured surface that is less than the textured surface of the medical device implant with one or more of the following measurements: an arithmetical mean height value (Sa) below about 3.0 μm and a developed interfacial area ratio (Sdr) above about 1.0 and a density of peaks (Spd) above about $1\times10^6$ peaks/mm$^2$. The medical device implant textured surface may further include a texture aspect ratio (Str) above about 0.6 and/or the textured surface may have a maximum height value (Sz) below about 40 μm. When in use as in a medical treatment, such a medical device implant produces one or more of the following functional outcomes as compared to an equivalent medical device implant in equivalent use not having a texture according the above measurements: reduction of the fibrous capsule layer thickness in a mammal by at least 15% and more preferably by at least 40%; reduction of fibrous capsule layer density in a mammal by at least 30% and more preferably by at least 50%; increase in fibroblast viability in vitro by at least 25% and more preferably by at least 50%.

TABLE C

Capsule Thickness and Density Measurements

| Example | Material | 4 weeks Total Thickness μm | Inflammatory Layer μm | Fibrous Layer μm | Capsule Density (normalized chromatic saturation relative to flat) % | 17 weeks Total Thickness μm | Inflammatory Layer μm | Fibrous Layer μm | Capsule Density (normalized chromatic saturation relative to flat) % |
|---|---|---|---|---|---|---|---|---|---|
| CE F | PDM_F | 209 | 39 | 170 | — | 270 | 33 | 237 | — |
| CE G | SilkSurface ®, SS | 217 | 71 | 146 | 120 | n.d. | n.d. | n.d. | n.d. |
| CE H | SPCU_F | 336 | 107 | 229 | — | 348 | 98 | 250 | — |
| CE I | PCU_F | 189 | 50 | 138 | — | 243 | 64 | 179 | — |
| CE J | PP_F | 266 | 82 | 184 | — | 318 | 53 | 265 | — |
| 1f | SPCU_1 | 330 | 170 | 161 | 64 | 335 | 93 | 242 | 70 |
| 1g | PCU_1 | 183 | 101 | 83 | 46 | 286 | 66 | 220 | 45 |
| 1h | PP_1 | 278 | 118 | 160 | 43 | 354 | 84 | 270 | 66 |
| 3f | SPU_3 | 334 | 181 | 152 | 66 | 368 | 86 | 282 | 74 |
| 3g | PCU_3 | 215 | 102 | 113 | 45 | 272 | 78 | 194 | 59 |
| 3h | PP_3 | 245 | 107 | 138 | 48 | 354 | 84 | 270 | 67 | n.d. = not determined

Figure 11:
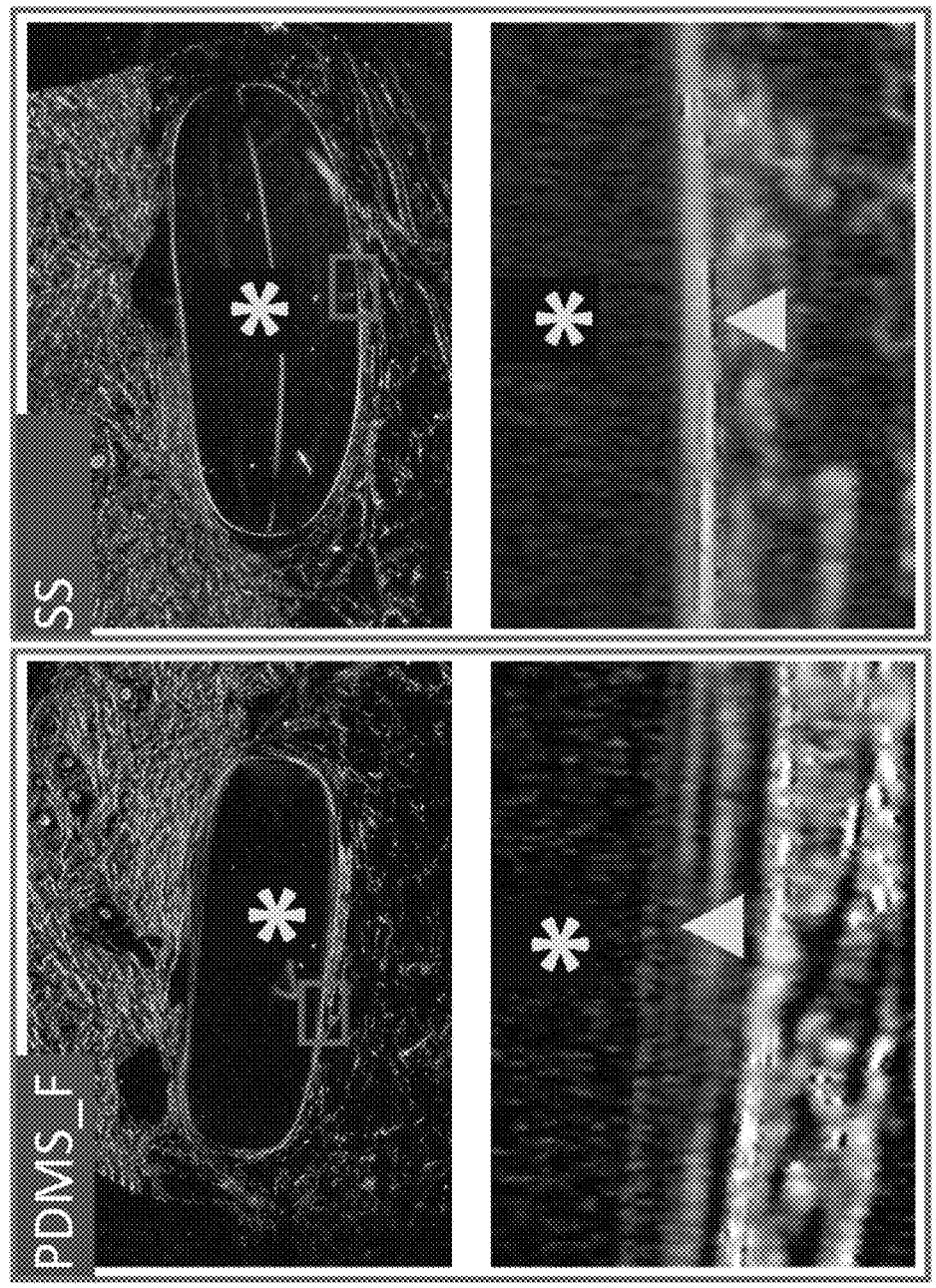
FIG. 11 are representative histological polarized micrographs depicting typical fibrous capsules formed around flat PDMS (PDMS_F) and SilkSurface® (SS) implants at 4 weeks. Stars denote the implants, and triangles denote the capsule immediately apposed to the implant surface. Micrographs were captured at 0.4× (top row) and 20× (bottom row) magnifications according to one embodiment of the present invention.

10). This modulation of tissue response and soft tissue repair demonstrate important benefits of the embodied microstructured surfaces for reducing capsular contracture of polymeric medical implants. In comparison, the capsule density of SilkSurface® implants, according to chromatic saturation, was on average 20% greater than flat PDMS at 4 weeks (i.e. SS=120% relativized versus the normalized chromatic saturation level of PDMS_F at 4 weeks; Table C). This result was further corroborated by polarized light microscopy which showed a similar collagen dense layer immediately apposed and highly aligned to the implant surface for both SS and PDMS_F implants (FIG. 11). Taken together, these results illustrate a unique benefit of the embodied microstructured architectures of embodiments of the present invention versus the flat and the SilkSurface® surface textures to more potently reduce capsular contracture.

One embodiment of the present invention provides for a medical device implant, for example breast implants, having a textured surface area such that when implanted in a patient or used in-vivo provides for reduction one or more of fibrous 3: In Vitro Performance Example 3.A—Cell Culture Human CD14+ monocytes (Cat. #2W-400A, Poeitics™ Lonza) were cultured on the surface of microstructured and flat sample discs for up to 25 days. Discs were placed in suspension culture 48-well plates (one disc per well) and fixed to the bottom of the well using silicone O-rings. Immediately prior to seeding cells, discs were incubated in 500 μl culture medium for up to 2 hours at 37 C, 5% $CO_2$ to equilibrate the discs to culture conditions. For the purpose of this macrophage study, the culture medium consisted of the following ingredients: 25 ng/mL human recombinant macrophage colony stimulating factor (M-CSF; Cat. #300-25-10 UG, Peprotech), 10% (v/v) fetal calf serum ("FCS", Cat. #SH30080.03, HyClone GE Health), 1% (v/v) penicillin streptomycin ("P-S", Gibco), all contained in Minimum Essential Medium-a ("MEM-α", Cat.#BE02-002F, Lonza). On the day of seeding, cells were gently thawed and resuspended in culture medium, according to the manufacturer's instructions, then further diluted in culture medium to a concentration of 550,000 cells in 500 µl. From this cell stock, 500 µl cell suspension was carefully pipetted on the surface of each disc, then the containing multiwell plates were transferred to culture incubators and left undisturbed for the cells to attach to the discs. Culture media was completely removed and replaced with 500 µl fresh, prewarmed media every 3-4 days. The removed culture media was collected on medium refreshment days—denoted, conditioned media—centrifuged to remove cellular material, and immediately stored at −80° C. until further use.

Separately, human dermal fibroblasts (Cat #: CC-2511 Lonza) were cultured in tissue culture treated 96-well plates for up to 7 days. Culture medium used for fibroblast cultures consisted of 10% FCS, 1% P-S, and MEM-α. Leading up to the study, cells were expanded in T75 culture flasks and subpassaged between 4 and 6 times upon reaching 80% confluence to create a cell stock with sufficient cell number for the study. On the day of seeding, cells were trypsinized in 2.5% trypsin-EDTA and resuspended at a density of 80,000 cells/ml. Cells were seeded in each well at a density of 8,000 cells in 100 µl medium. After 1 day of culture, culture media was completely removed and replaced with 50 µl fresh, prewarmed culture media per culture well. An additional 50 µl of prewarmed macrophage-derived conditioned media was supplemented to each culture well. After 2 days of culture, an additional 50 µl of prewarmed macrophage-derived conditioned media was supplemented to each culture well. After 3 days of culture, an additional 50 µl of prewarmed macrophage-derived conditioned media and 50 µl of prewarmed fresh culture media was supplemented to each culture well, without any media removal. The culture was maintained through 7 days culture. In this way, human fibroblasts were exposed to a sustained dose of secreted paracrine factors produced by macrophages cultured on the sample discs in the experiment described above. Cells were cultured in incubators maintained at 37° C., 5% $CO_2$.

The cell studies were repeated at least twice to ensure reproducibility and consistency of results.

Example 3.B—Cell Viability

Cell viability was measured using the PrestoBlue Cell Viability assay (Cat. #A13261, Invitrogen) following the manufacturer's instructions. On the day of measurement, culture media was removed from the culture well and replaced with 250 µl 5% (v/v) PrestoBlue prewarmed media, diluted in fresh culture medium (10% FCS, 1% P-S, MEM-α). Cells were incubated in PrestoBlue media for 2 hours at 37° C., 5% $CO_2$ to ensure sufficient signal. The incubated PrestoBlue media was then individually sampled to the wells of a black, opaque 96-well plate (100 µl sample per well) for fluorescent measurement using a Clariostar Plus multimode plate reader (560 nm/590 nm, excitation/emission wavelengths). Duplicate samples per culture well were measured, and averaged across replicate cell-culture wells. Mean relative fluorescent unit values, rounded to the nearest 1 unit, were reported.

Example 3.0—May-Grünwald-Giemsa Staining

May-Grünwald-Giemsa (MGG) staining is a Romanowsky-type, polychromatic stain routinely used for hematology and diagnostic cytopathology. At specific culture time-points, cell culture media was fully removed, cells were washed with neutral phosphate buffered saline (PBS) containing calcium and magnesium (Cat. #14040141 Gibco), and fixed in 2.5% glutaraldehyde diluted in neutral PBS for at least one hour at room temperature (RT). Fixative was removed, and cells were further fixed and permeabilized by incubating in methanol for 10 minutes at RT. Methanol was removed, and cells were stained according to the following protocol: 5 minute incubation in May-Grünwald solution (diluted 1:1 v/v in pH 6.8 PBS; Cat. #MG500, Sigma-Aldrich); 3 minute incubation in pH 6.8 PBS buffer; 30 minute incubation in Giemsa solution (diluted 1:9 v/v in pH 6.8 PBS buffer; Cat. #48900, Sigma-Aldrich); washed 3 minutes in pH 6.8 PBS buffer; dried. All staining steps were conducted at RT. Imaging of the stained cells was conducted using a Nikon SMZ25 stereomicroscope.

Example 3.D—Scanning Electron Microscopy

Scanning electron microscopy (SEM) of cultured cells was performed as follows. At specific culture time-points, cell culture media was fully removed, cell-seed samples were washed with neutral phosphate buffered saline (PBS) containing calcium and magnesium (Cat. #14040141, Gibco), and fixed in 2.5% glutaraldehyde diluted in neutral PBS for at least one hour at RT. Fixative was removed, and samples were further dehydrated in a graded series of ethanol (e.g. 50%, 60%, 70%, 80%, 90%, 100%, 100% ethanol). Samples were further dehydrated in an automated critical point dryer (e.g. Leica EM CPD300 machine) and affixed to conductive metal pins using carbon tape. Samples were sputter-coated with a nanolayer of gold, approximately 10 nm thick, and then imaged using a scanning electron microscope (SEM, e.g. Philips XL-30, JEOL IT200). Micrographs were captured at various magnification levels ranging from 500× to 5,000× with typical acceleration voltage of 10-15 keV.

Example 3.E—Results of the In Vitro Performance

The behavior and response of human macrophages cultured on the surface of microstructured and flat polymeric discs was characterized in vitro. Human CD14+ monocytes were used as a relevant model for studying the foreign body response, in that monocytes differentiate into macrophages upon adhesion with a substrate, and macrophages are the body's primary line of defense against foreign bodies such as medical implants. Macrophages exist in nearly every tissue of the body and are the progeny of monocytes arising from the bone marrow.

Figure 12:
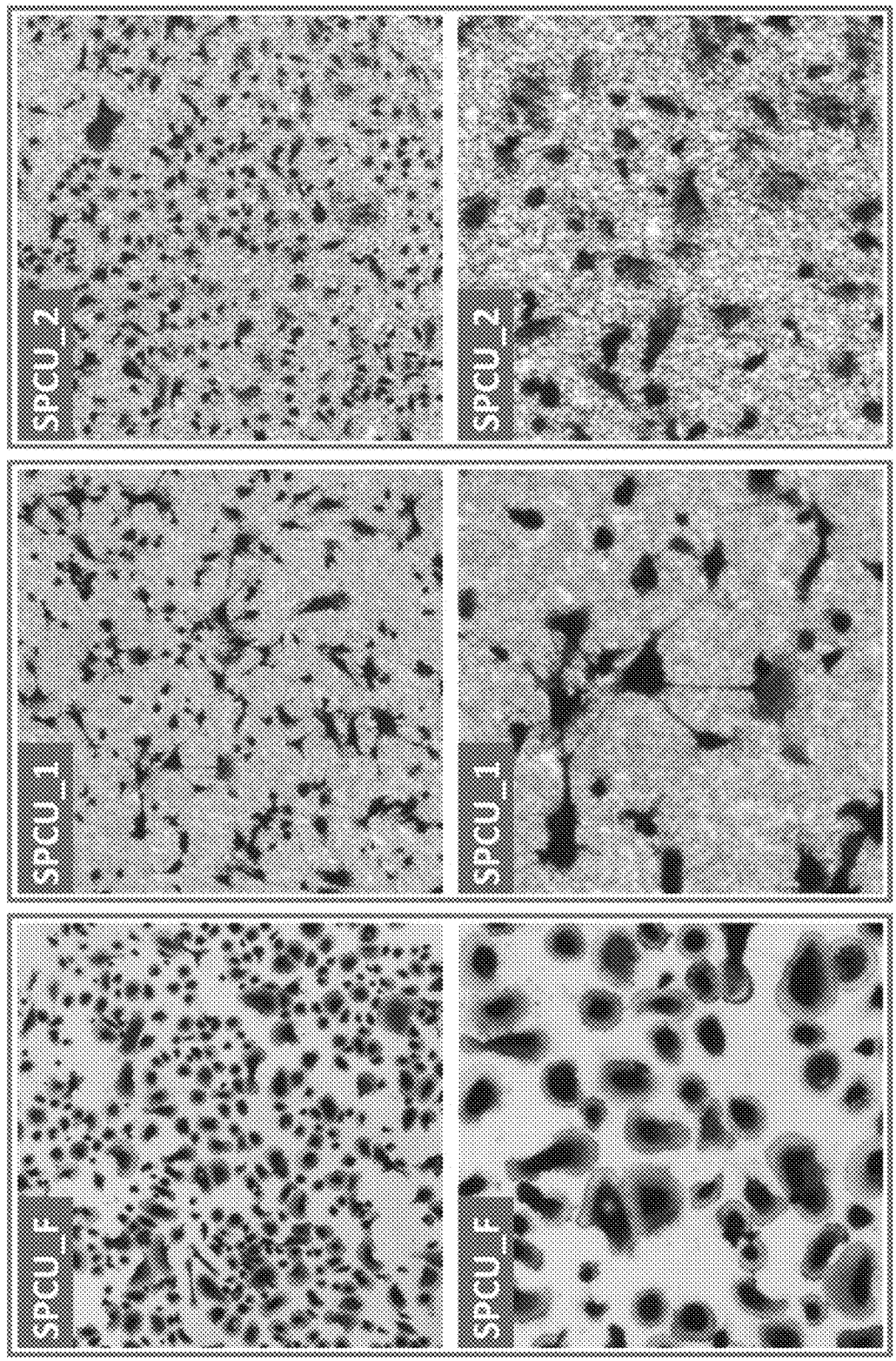
FIG. 12 are light micrographs depicting human macrophages cultured on flat and microstructured polymers for 21 days. Cells were stained with May-Grünwald-Giemsa staining, which appears blue and pink in the original color images. Micrographs were captured at 4× (top row) and 10× (bottom row) magnifications according to one embodiment of the present invention.
Figure 13:
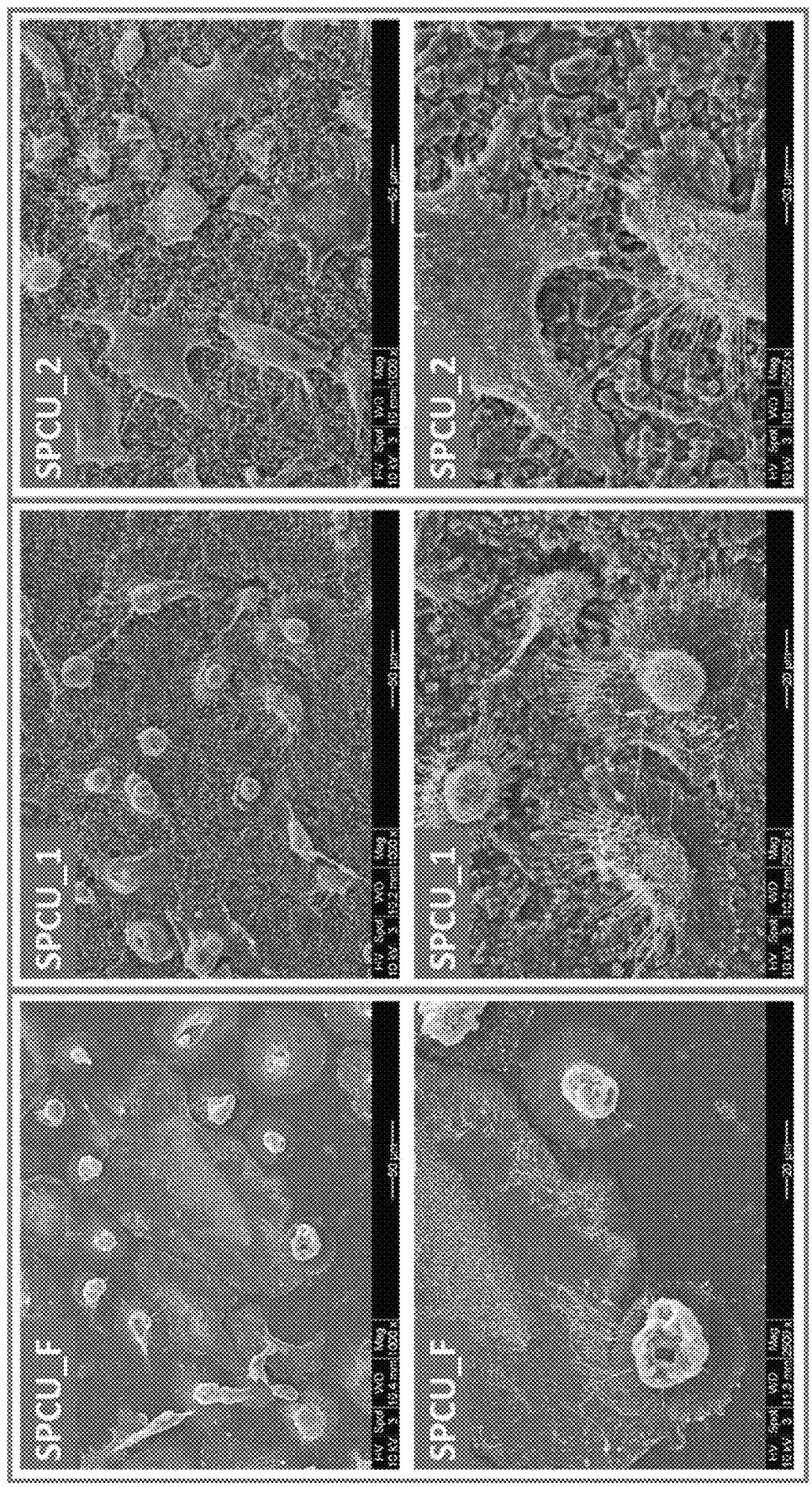
FIG. 13 are scanning electron micrographs depicting human macrophages cultured on flat and microstructured polymers for 21 days. Micrographs were captured at 1,000× (top row) and 2,500× (bottom row) magnifications according to one embodiment of the present invention.

Microstructured and flat polymer discs were prepared as described in the methods and used for the in vitro study according to Tables D and E. Culture on microstructured samples was shown to profoundly change the macrophage morphology at 21 days based on MGG staining (FIG. 12) and SEM (FIG. 13). From MGG staining, it was observed that macrophage shape on flat samples was predominantly roundish, and well spread; in comparison, macrophages cultured on microstructured surfaces were more irregularly shaped, less round, and generally less spread. It is particularly noted that macrophages cultured on microstructured surfaces—especially surfaces with TCP1 microstructure, e.g. SPCU_1, PCU_1, and PP_1—tended to create more cell-cell junctions, linked by cellular filopodia connections. This resembled a more activated state. In SEM, differences were also noted. Specifically, macrophages cultured on flat tended to be round and well spread, sometimes 100s of microns in length, suggesting cells have fused to form giant cells. It is typical for macrophages cultured on flat surfaces to have a spheroid apical morphology resembling a doorknob. In comparison, macrophages cultured on micro structured surfaces appeared generally less spread out. On TCP1 microstructured surfaces (e.g. SPCU_1, PCU_1, and PP_1), macrophage size was generally less than 60 micron across; on TCP2 microstructured surfaces (e.g. SPCU_2, PCU_2, and PP_2), macrophage size was generally less than 100 micron across. Most cells cultured on TCP1 microstructured surfaces possessed a spheroid apical morphology resembling a doorknob, while cells cultured on TCP2 microstructured surfaces less often possessed this morphology but rather appear flatter. Taken together, these results indicate that microstructured polymeric surfaces affect macrophage morphology and phenotype in distinct ways, and that the specific size scale of microstructural features plays a role in this.

Macrophage viability after culture for 3, 10, and 21 days on microstructured and flat polymeric discs was measured using the PrestoBlue assay (Table D). No consistent differential effects of the surface structure on cell viability across the various polymers tested were discernible. These results indicate that microstructured polymeric surfaces are not cytotoxic to cells, nor do they promote more or less cell adhesion than respective flat surfaces.

During macrophage culture on microstructured and flat polymer discs, conditioned medium containing macrophage-secreted paracrine factors was collected and supplemented into fibroblast cultures to study the effects on fibroblasts response. This type of in vitro model is often used in the art to study the interplay between macrophages and fibroblasts in the foreign body response and fibrosis. Fibroblasts are the principal constructor and resident of the fibrous capsule that forms around a foreign body; moreover, given the relevant paracrine signals, fibroblasts can differentiate into myofibroblasts which are the main contractile agent causing capsular contracture. It is known in the literature that when fibroblasts are proliferating—evidenced by high viability—they are not also differentiating into myofibroblasts (DOI: 10.1096/fj.03-0699com); therefore, it is useful to study fibroblast proliferation, as a function of viability, to determine their propensity to promote capsular contracture.

TABLE D

Macrophage viability as measured by the PrestoBlue assay (values: mean relative fluorescent units)

| Example | Material | Day 3 | Day 10 | Day 21 |
|---|---|---|---|---|
| CE K | PDMS_F | 39465 | 58130 | 49725 |
| CE L | SPCU_F | 32306 | 43429 | 58983 |
| CE M | PCU_F | 27778 | 35132 | 45324 |
| CE N | PP_F | 57465 | 62681 | 67889 |
| 1i | SPCU_1 | 26642 | 43557 | 54571 |
| 1j | PCU_1 | 18026 | 21083 | 48580 |
| 1k | PP_1 | 53515 | 91454 | 101282 |
| 2i | SPCU_2 | 31572 | 62264 | 72934 |
| 2j | PCU_2 | 12788 | 28737 | 40926 |
| 2k | PP_2 | 46328 | 95592 | 96663 |

Fibroblast viability was measured after culture for 7 days using the PrestoBlue assay (Table E). During the culture period, fibroblasts were exposed to macrophage-derived conditioned medium (MP CM) as described here above in the methods. Cell viability is considered to be a proxy measure of cell proliferation because higher cell viability correlates with higher cell proliferation. After treatment with MP CM derived from microstructured polymer surfaces, mean fibroblast viability was generally higher than from MP CM treatment derived from flat surfaces. This effect was evident for all polymer groups, illustrating a conserved response irrespective of material chemistry. This effect was also consistent for MP CM collected at various macrophage culture time points, e.g. after 3 days, 10 days, 17 days, or 21 days. The promotive effect on fibroblast viability was most pronounced and consistently evident from MP CM treatment derived from TCP1 microstructured polymer surfaces (e.g. SPCU_1, PCU_1, and PP_1). Fibroblast viability generally also increased following treatment with MP CM derived from TCP2 microstructured polymer surfaces (e.g. SPCU_2, PCU_2, and PP_2) versus MP CM derived from flat polymer surfaces (e.g. SPCU_F, PCU_F, and PP_F), although to a lesser extent. While fibroblast viability increases following treatment with MP CM derived from microstructured surfaces, a positive effect on capsular contracture can be expected based on the literature. These results point to a protective paracrine effect elicited by macrophages cultured on microstructured surfaces, with increasing potency as the scale of microstructural features decreases (e.g. TCP1 vs. TCP2).

TABLE E

Fibroblast viability as measured by the PrestoBlue assay (values: mean relative fluorescent units)

| Example | Material | Day 3 | Day 10 | Day 17/21 |
|---|---|---|---|---|
| CE O | SPCU_F | 78723 | 49419 | 69009 |
| CE P | PCU_F | 126561 | 120306 | 113934 |
| CE Q | PP_F | 126111 | 125663 | 117034 |
| 1l | SPCU_1 | 98344 | 97572 | 105326 |
| 1m | PCU_1 | 132957 | 133250 | 123498 |
| 1n | PP_1 | 138106 | 136937 | 121054 |
| 2l | SPCU_2 | 75142 | 73229 | 91261 |
| 2m | PCU_2 | 132798 | 124230 | 119085 |
| 2n | PP_2 | 133313 | 129640 | 121162 |

Note that in the specification and claims, "about" or "approximately" means within twenty percent (20%) of the numerical amount cited. Although embodiment of the invention have been described in detail with particular reference to these embodiments, other embodiments can achieve the same results. For example, the processing steps can be automated and carried out with an appropriately programmed processor. In at least one embodiment, and as readily understood by one of ordinary skill in the art, the system and process according to the invention will include a general or specific purpose computer or distributed system programmed with computer software implementing the steps described above, which computer software may be in any appropriate computer language, including C++, FORTRAN, BASIC, Java, assembly language, microcode, distributed programming languages, etc. The apparatus may also include a plurality of such computers/distributed systems (e.g., connected over the Internet and/or one or more intranets) in a variety of hardware implementations. For example, data processing can be performed by an appropriately programmed microprocessor, computing cloud, Application Specific Integrated Circuit (ASIC), Field Programmable Gate Array (FPGA), or the like, in conjunction with appropriate memory, network, and bus elements.

Variations and modifications of the present invention will be obvious to those skilled in the art and it is intended to cover in the appended claims all such modifications and equivalents. The entire disclosures of all references, applications, patents, and publications cited above are hereby incorporated by reference.

The invention claimed is:

1. A medical implant adapted for placement inside of or on a body surface of a subject, the medical implant comprising:
a textured surface which, in use, directly contacts one or more of biological fluid, tissue, and cells of the subject, the textured surface having an arithmetical mean height value (Sa) below 3.0 μm, a developed interfacial area ratio (Sdr) above 1.0, and a density of peaks (Spd) above $1\times10^6$ peaks/mm$^2$, wherein the Sa, the Sdr, and the Spd are measured according to ISO 25178 using a Gaussian low pass S-filter with a nesting index value of at least 0.25 μm, and
whereby the contact effects one or more of: limiting fibrosis, limiting foreign body response, resisting bacterial and viral adhesion and proliferation, resisting blood coagulation and thrombosis, promoting biological adhesion and integration of biological tissue, guiding cell differentiation, instructing cell migration, promoting cell survival, and perpetuating a selected cellular phenotype limiting fibrosis, with respect to the medical implant.

2. The medical implant of claim 1 wherein the textured surface has a texture aspect ratio (Str) above 0.6.

3. The medical implant of claim 1 wherein the textured surface has a maximum height value (Sz) below 40 μm.

4. The medical implant of claim 1 wherein the textured surface comprises a biocompatible polymeric material.

5. The medical implant of claim 4 wherein the biocompatible polymeric material is a polyester, a polyurethane, an organosilicon, or a polyolefin.

6. The medical implant of claim 1, wherein the implant is one of: a breast implant, a cardiac or cardiovascular implant, a surgical mesh, a neurostimulation lead, an ophthalmic implant, a urological implant, or a biosensor.

7. The medical implant of claim 1, wherein the textured surface is an entire surface of the medical implant.

8. The medical implant of claim 1, wherein the textured surface is on an outer surface of the medical implant.

9. The medical implant of claim 1, wherein limiting fibrosis comprises one or both of (i) a reduction of fibrous capsule layer thickness in the subject by at least 15%; and (ii) a reduction of fibrous capsule layer density in the subject by at least 30%, after four weeks and relative to a second medical implant without the textured surface.

10. A process for preparing the medical implant of claim 1, the process comprising:
providing a microstructured template, wherein the microstructured template comprises a textured surface with an arithmetical mean height value (Sa) below 3.0 μm, a developed interfacial area ratio (Sdr) above 1.0, and a density of peaks (Spd) above about $1\times10^6$ peaks/mm$^2$, wherein the Sa, the Sdr, and the Spd are measured according to ISO 25178 using a Gaussian low pass S-filter with a nesting index value of at least 0.25 μm;
covering the microstructured template with a biocompatible polymeric material that is a solid or a liquid;
conforming the biocompatible polymeric material to textural contours of the template using one or more of elevated temperature, pressure, or vacuum;
processing the biocompatible polymeric material, when provided as liquid, until solid; and
separating a textured biocompatible polymeric material from the microstructured template.

11. A microstructured template used for preparing the medical implant of claim 1, the microstructured template comprising:
a textured surface with an arithmetical mean height value (Sa) below 3.0 μm and a developed interfacial area ratio (Sdr) above 1.0 and a density of peaks (Spd) above $1\times10^6$ peaks/mm$^2$, wherein the Sa, the Sdr, and the Spd are measured according to ISO 25178 using a Gaussian low pass S-filter with a nesting index value of at least 0.25 μm.

12. The microstructured template of claim 11, wherein the template comprises a sintered ceramic material.

13. The microstructured template of claim 12 wherein the sintered ceramic material is tricalcium phosphate (TCP).

14. A method of treating a mammal in need of treatment comprising:
implanting the medical implant of claim 1 into the mammal.

15. The method of claim 14 wherein the mammal is a human.

16. The method of claim 14, wherein the medical implant is one of: a breast implant, a cardiac or cardiovascular implant, a surgical mesh, a neurostimulation lead, an ophthalmic implant, a urological implant, or a biosensor.

17. The method of claim 14, wherein the treatment is cosmetic breast augmentation or reconstruction, and the medical implant is a breast implant.

18. The method of claim 14, wherein the medical implant comprises a biocompatible polymer.

19. The method of claim 14, wherein, in use, the medical implant provides for at least one of i) reducing a fibrous capsule density, ii) reducing a fibrous capsule thickness, or iii) increasing a fibroblast viability on the medical implant textured surface that is in contact with tissue as compared to a second medical implant in use under the same conditions and of the same dimensions with no textured surface or a textured surface selected from one of a) an arithmetical mean height value (Sa) above about 3.0 μm and a developed interfacial area ratio (Sdr) below about 1.0 and a density of peaks (Spd) below about $1\times10^6$ peaks/mm$^2$; b) a surface that has an arithmetical mean height value (Sa) above about 3.0 μm and a developed interfacial area ratio (Sdr) below about 1.0, or c) a surface that has an arithmetical mean height value (Sa) above about 3.0 μm and a density of peaks (Spd) below about $1\times10^6$ peaks/mm$^2$.

20. A medical device adapted for placement inside of or on a body surface of a subject, the medical device comprising:
a textured surface having an arithmetical mean height value (Sa) of from 0.3 to 5.0 μm, a developed interfacial area ratio (Sdr) above 1.0, a density of peaks (Spd) above $1\times10^6$ peaks/mm$^2$, and a surface root mean square gradient (Sdq) of from 1.0 to 8.0, wherein the Sa, Sdr, Spd, and Sdq are measured according to ISO 25178 using a Gaussian low pass S-filter with a nesting index value of at least 0.25 μm, and
wherein, in use, the textured surface directly contacts one or more of biological fluid, tissue, and cells of the subject.

* * * * *